US010058552B2

(12) United States Patent
Renshaw et al.

(10) Patent No.: US 10,058,552 B2
(45) Date of Patent: Aug. 28, 2018

(54) COMBINATION OF CREATINE, AN OMEGA-3 FATTY ACID, AND CITICOLINE

(71) Applicant: University of Utah Research Foundation, Salt Lake City, UT (US)

(72) Inventors: Perry Renshaw, Salt Lake City, UT (US); Deborah Yurgelun-Todd, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/117,143

(22) PCT Filed: Feb. 6, 2015

(86) PCT No.: PCT/US2015/014856
§ 371 (c)(1),
(2) Date: Aug. 5, 2016

(87) PCT Pub. No.: WO2015/120299
PCT Pub. Date: Aug. 13, 2015

(65) Prior Publication Data
US 2017/0165264 A1 Jun. 15, 2017

Related U.S. Application Data

(60) Provisional application No. 61/937,328, filed on Feb. 7, 2014.

(51) Int. Cl.
*A61K 31/513* (2006.01)
*A61K 31/19* (2006.01)
*A61K 31/197* (2006.01)

(52) U.S. Cl.
CPC ............ *A61K 31/513* (2013.01); *A61K 31/19* (2013.01); *A61K 31/197* (2013.01)

(58) Field of Classification Search
None
See application file for complete search history.

(56) References Cited

U.S. PATENT DOCUMENTS

| 6,503,951 | B2  | 1/2003  | Pischel et al. |
| 6,964,969 | B2* | 11/2005 | McCleary ............ A61K 31/00 424/752 |
| 8,575,219 | B2  | 11/2013 | Renshaw |
| 2002/0182196 | A1 | 12/2002 | McCleary |
| 2005/0129710 | A1 | 6/2005 | Renshaw et al. |
| 2005/0143350 | A1 | 6/2005 | Seed |
| 2006/0216251 | A1 | 9/2006 | Morariu |
| 2008/0132472 | A1 | 6/2008 | Renshaw |
| 2010/0197628 | A1 | 8/2010 | Renshaw et al. |
| 2013/0281410 | A1 | 10/2013 | Renshaw |

FOREIGN PATENT DOCUMENTS

| CN | PCT/US2015/014856 | 2/2015 |
| EP | 15746527.9 | 2/2015 |
| JP | 2016-550629 | 2/2015 |
| KR | PCT/US2015/014856 | 2/2015 |
| WO | WO-2004/000297 A1 | 12/2003 |
| WO | WO-2005/086619 A2 | 9/2005 |
| WO | PCT/US2011/055399 | 10/2011 |
| WO | WO-2012/048243 A2 | 4/2012 |
| WO | PCT/US2015/014856 | 2/2015 |

OTHER PUBLICATIONS

U.S. Appl. No. 61/937,328, filed Feb. 7, 2014, Renshaw et al.
International Preliminary Report on Patentability dated Aug. 9, 2016 for Application No. PCT/US2015/014856, which was filed on Feb. 6, 2015 and published as WO 2015/120299 on Aug. 13, 2015 (Inventor—Renshaw et al; Applicant—University of Utah) (7 pages).
Allen, P.J., et al., "Chronic creatine supplementation alters depression-like behavior in rodents in a sex-dependent manner," Neuropsychopharmacology, 35(2): 534-546 (2010).
Barbui, C., et al., "Selective serotonin reuptake inhibitors and risk of suicide: A systematic review of observational studies," CMAJ, 180(3): 291-297 (2009).
Barratt, A, et al., "Tips for learners of evidence-based medicine: 1. Relative risk reduction, absolute risk reduction and number needed to treat," CMAJ, 171(4): 353-358 (2004).
Bergemann, E.R. and Boles, R.G., "Maternal inheritance in recurrent early-onset depression," Psychiatr Genet, 20(1): 31-34 (2010).
Birmaher, B, et al., "Childhood and adolescent depression: A review of the past 10 years. Part i," J Am Acad Child Adolesc Psychiatry, 35(11): 1427-1439 (1996).
Birmaher, B., et al., "Practice parameter for the assessment and treatment of children and adolescents with depressive disorders," J Am Acad Child Adolesc Psychiatry, 46(11): 1503-1526 (2007).
Brammer, M., "The role of neuroimaging in diagnosis and personalized medicine—current position and likely future directions," Dialogues Clin Neurosci, 11(4): 389-396 (2009).
Brent, D., et al., "Switching to another SSRI or to venlafaxine with or without cognitive behavioral therapy for adolescents with SSRI-resistant depression: the TORDIA randomized controlled trial," JAMA, 299(8): 901-13 (2008).
Bridge, J.A., et al., "Placebo response in randomized controlled trials of antidepressants for pediatric major depressive disorder," Am J Psychiatry, 166: 42-49 (2009).
Brosnan, J.T. and Brosnan, M.E., "Creatine: Endogenous metabolite, dietary, and therapeutic supplement," Annu Rev Nutr, 27:241-261 (2007).
De Leon, J., "Pharmacogenomics: The promise of personalized medicine for cns disorders," Neuropsychopharmacology, 34(1): 159-172 (2009).

(Continued)

*Primary Examiner* — Brian J Davis
(74) *Attorney, Agent, or Firm* — Ballard Spahr LLP

(57) ABSTRACT

In one aspect, the invention relates to compositions comprising at least one creatine or creatine analog, at least one omega-3 fatty acid, and citicoline analogs. Also disclosed are methods of using same, alone or in combination with other agents, to treat depression disorders and associated maladies. Also disclosed are methods of using same, alone or in combination with other agents, to improve neuropsychological performance. Also disclosed are methods of using same, alone or in combination with other agents, to improve complexion. This abstract is intended as a scanning tool for purposes of searching in the particular art and is not intended to be limiting of the present invention.

12 Claims, 4 Drawing Sheets

(56) References Cited

OTHER PUBLICATIONS

Drevets, W.C., et al., "Brain structural and functional abnormalities in mood disorders: Implications for neurocircuitry models of depression," Brain Struct Funct, 213(1-2): 93-118 (2008).
Dubicka, B., et al., "Suicidal behaviour in youths with depression treated with new-generation antidepressants: Meta-analysis," Br J Psychiatry, 189:393-398 (2006).
Eaton, D.K., et al., "Youth risk behavior surveillance—united states, 2009," MMWR Surveill Summ, 59(5): 1-142 (2010).
Fattal, O., et al., "Psychiatric comorbidity in 36 adults with mitochondrial cytopathies," CNS Spectr, 12(6): 429-438 (2007).
Fergusson, D.M. and Woodward, L.J., "Mental health, educational, and social role outcomes of adolescents with depression," Arch Gen Psychiatry, 59(3): 225-231 (2002).
Fergusson, D.M., et al., "Subthreshold depression in adolescence and mental health outcomes in adulthood," Arch Gen Psychiatry, 62(1): 66-72 (2005).
Fombonne, E., et al., "The maudsley long-term follow-up of child and adolescent depression. 1. Psychiatric outcomes in adulthood," Br J Psychiatry, 179: 210-217 (2001a).
Fombonne, E., et al., "The maudsley long-term follow-up of child and adolescent depression. 2. Suicidality, criminality and social dysfunction in adulthood," Br J Psychiatry, 179: 218-223 (2001b).
Garrison, C.Z., et al., "Incidence of major depressive disorder and dysthymia in young adolescents," J Am Acad Child Adolesc Psychiatry, 36(4): 458-465 (1997).
Gerber, A.J. and Peterson, B.S., "Applied brain imaging," J Am Acad Child Adolesc Psychiatry, 47(3): 239 (2008).
Gerretsen, P., et al., "The intersection of pharmacology, imaging, and genetics in the development of personalized medicine," Dialogues Clin Neurosci, 11(4): 363-376 (2009).
Goodman, W.K., ""Research on biomarkers for mental disorders. National Institute of Mental Health (2009). http://www.nimh.nih.gov/research-funding/grants/conceptclearances/.
Goodman, W.K., et al., "Risk of adverse behavioral effects with pediatric use of antidepressants," Psychopharmacology (Berl), 191(1): 87-96 (2007).
Gorman, J.M., "Gender differences in depression and response to psychotropic medication," Gend Med, 3(2): 93-109 (2006).
Gualano, B., et al., "Exploring the therapeutic role of creatine supplementation," Amino Acids, 38(1): 31-44 (2010) .
Guidance for industry. E6 good clinical practice: Consolidated guidance, Food and Drug Administration, Rockville, MD (1996).
Guy,W., ECDEU assessment manual for psychopharmacology, revised, U.S. Dept. of Health, Education, and Welfare, Public Health Service, Alcohol, Drug Abuse, and Mental Health Administration, National Institute of Mental Health, Psychopharmacology Research Branch, Division of Extramural Research Programs, Rockville, MD (1976).
Hammad, T.A., et al., "Suicidality in pediatric patients treated with antidepressant drugs," Arch Gen Psychiatry, 63(3): 332-339 (2006).
Hankin, B.L., et al., "Development of depression from preadolescence to young adulthood: Emerging gender differences in a 10-year longitudinal study," J Abnorm Psychol, 107(1): 128-140 (1998).
Harris, G., "F.D.A. Requiring suicide studies in drug trials," New York Times, Jan. 24, 2008, p. A1 (2008).
Hetrick, S., et al., "Selective serotonin reuptake inhibitors (ssris) for depressive disorders in children and adolescents," Cochrane Database Syst Rev, (3):31 (2007).
Holsboer, F., "How can we realize the promise of personalized antidepressant medicines?" Nat Rev Neurosci, 9(8): 638-646 (2008).
Iosifescu, D.V. and Renshaw, P.F., "31 p-magnetic resonance spectroscopy and thyroid hormones in major depressive disorder: Toward a bioenergetic mechanism in depression?" Harv Rev Psychiatry, 11(2): 51-63 (2003).
Iosifescu, D.V., et al., "Brain bioenergetics and response to triiodothyronine augmentation in major depressive disorder," Biol Psychiatry, 63(12): 1127-1134 (2008).

Jost, C.R., et al., "Creatine kinase b-driven energy transfer in the brain is important for habituation and spatial learning behaviour, mossy fibre field size and determination of seizure susceptibility," Eur J Neurosci, 15(10): 1692-1706 (2002).
Kaptsan, A., et al., "Lack of efficacy of 5 grams daily of creatine in schizophrenia: A randomized, double-blind, placebo-controlled trial," J Clin Psychiatry, 68(6): 881-884 (2007).
Kasahara, T., et al., "Mice with neuron-specific accumulation of mitochondrial DNA mutations show mood disorder-like phenotypes," Mol Psychiatry, 11(6): 577-593, 523 (2006).
Kato, T., "Mitochondrial dysfunction as the molecular basis of bipolar disorder: Therapeutic implications," CNS Drugs, 21(1): 1-11 (2007).
Kaufman, J., et al., "Schedule for affective disorders and schizophrenia for school-age children-present and lifetime version (k-sads-pl): Initial reliability and validity data," J Am Acad Child Adolesc Psychiatry, 36(7): 980-988 (1997).
Kessler, R.C. and Walters, E.E., "Epidemiology of dsm-iii-r major depression and minor depression among adolescents and young adults in the national comorbidity survey," Depress Anxiety, 7(1): 3-14 (1998).
Kessler, R.C., "Sex and depression in the national comorbidity survey. I: Lifetime prevalence, chronicity and recurrence," J Affect Disord, 29(2-3): 85-96 (1993).
Klempan, T.A., et al., "Altered expression of genes involved in atp biosynthesis and gabaergic neurotransmission in the ventral prefrontal cortex of suicides with and without major depression," Mol Psychiatry, 14(2): 175-189 (2009).
Koene, S., et al., "Major depression in adolescent children consecutively diagnosed with mitochondrial disorder," J Affect Disord, 114(1-3): 327-332 (2009).
Koshy, K.M., et al., "Interstitial nephritis in a patient taking creatine," N Engl J Med, 340(10): 814-815 (1999).
Kovacs, M., "Presentation and course of major depressive disorder during childhood and later years of the life span," J Am Acad Child Adolesc Psychiatry, 35(6): 705-715 (1996).
Kovacs, M., "The emanuel miller memorial lecture 1994. Depressive disorders in childhood: An impressionistic landscape," J Child Psychol Psychiatry, 38(3):287-298 (1997).
Leibenluft, E., ""Skating to where the puck will be: The importance of neuroimaging literacy in child psychiatry,""J Am Acad Child Adolesc Psychiatry, 47(11): 1213-1216 (2008).
Lewinsohn, P.M., et al., "Major depressive disorder in older adolescents: Prevalence, risk factors, and clinical implications," Clin Psychol Rev, 18(7): 765-794 (1998).
Lewinsohn P.M., et al., "Adolescent psychopathology: I. Prevalence and incidence of depression and other dsm-iii-r disorders in high school students," J Abnorm Psychol, 102(1): 133-144 (1993).
Lynch, F.L. and Clarke, G.N., "Estimating the economic burden of depression in children and adolescents," Am J Prey Med, 31(6 Suppl 1): S143-151 (2006).
Lyoo, I.K., et al., "Multinuclear magnetic resonance spectroscopy of high-energy phosphate metabolites in human brain following oral supplementation of creatine¬ monohydrate," Psychiatry Res, 123(2): 87-100 (2003).
Ma, J., et al., "Depression treatment during outpatient visits by U.S. Children and adolescents," J Adolesc Health, 37(6): 434-442 (2005).
Major depressive episode among youths aged 12 to 17 in the United States: 2004 to 2006, The NSDUH Report, Substance Abuse and Mental Health Services Administration, Washington, D.C. (2008).
McCauley, E., et al., "Depression in young people: Initial presentation and clinical course," J Am Acad Child Adolesc Psychiatry, 32(4): 714-722 (1993).
McLeish, M.J. and Kenyon, G.L., "Relating structure to mechanism in creatine kinase," Crit Rev Biochem Mol Biol, 40(1): 1-20 (2005).
Moller, H.J., et al., "Do ssris or antidepressants in general increase suicidality? Wpa section on Pharmacopsychiatry: Consensus statement," Eur Arch Psychiatry Clin Neurosci, 258 Auppl 3: 3-23 (2008).

(56) References Cited

OTHER PUBLICATIONS

Moore, C.M., et al., "Lower levels of nucleoside triphosphate in the basal ganglia of depressed subjects: A phosphorous-31 magnetic resonance spectroscopy study," Am J Psychiatry, 154(1): 116-118 (1997).
Moretti, A., et al., ""Affective disorders, antidepressant drugs and brain metabolism,"" Mol Psychiatry, 8(9): 773-785 (2003).
Newman, T.B., "A black-box warning for antidepressants in children?" N Engl J Med, 351(16): 1595-1598 (2004).
Olfson, M., et al., "Antidepressant drug therapy and suicide in severely depressed children and adults: A case-control study," Arch Gen Psychiatry, 63(8): 865-872 (2006).
Owens, P.L., et al., "Care of children and adolescents in U.S. Hospitals," Hcup fact books, vol AHRQ Publication No. 04-0004, Agency for Healthcare Research and Quality, Rockville, MD (2003).
Pavuluri, M.N. and Sweeney, J.A., "Integrating functional brain neuroimaging and developmental cognitive neuroscience in child psychiatry research," J Am Acad Child Adolesc Psychiatry, 47(11): 1273-1288 (2008).
Pine, D.S., et al., "Adolescent depressive symptoms as predictors of adult depression: Moodiness or mood disorder?" Am J Psychiatry, 156(1): 133-135 (1999).
Pollack BG, Citalopram: comprehensive review., Exp. Opin. Pharmacother. (2001) 2(4): 681-698.
Porsolt, R.D., et al., "Depression: A new animal model sensitive to antidepressant treatments," Nature, 266(5604): 730-732 (1977).
Posner, K., Columbia-suicide severity rating scale (c-ssrs). Center for Suicide Risk Assessment, Columbia University Medical Center (2010). http://cssrs.columbia.edu/index.html. Accessed May 15, 2010.
Posner, K., et al., "Columbia classification algorithm of suicide assessment (c-casa): Classification of suicidal events in the fda's pediatric suicidal risk analysis of antidepressants," Am J Psychiatry, 164(7): 1035-1043 (2007).
Posner, K., et al., "Suicidality classification project," Food and Drug Administration Psychopharmacologic Drugs Advisory Committee and the Pediatric Advisory Committee (2004). http://www.fds.gov/ohrms/dockets/ac/04/slides/2004-4065S1_06_FDA⌐Posner_files/frame.htm. Accessed Dec. 15, 2006.
Pritchard, N. R. and Kalra, P.A., "Renal dysfunction accompanying oral creatine supplements," Lancet, 351(9111): 1252-1253 (1998).
Puri, B.K., "Proton and 31-phosphorus neurospectroscopy in the study of membrane phospholipids and fatty acid intervention in schizophrenia, depression, chronic fatigue syndrome (myalgic encephalomyelitis) and dyslexia," Int Rev Psychiatry, 18(2): 145-147 (2006).
Rae, C., et al., "Oral creatine monohydrate supplementation improves brain performance: A double-blind, placebo-controlled, cross-over trial," Proc Biol Sci, 270(1529): 2147-2150 (2003).
Rango, M., et al., ""Energetics of 3.5 s neural activation in humans: A 31P mr spectroscopy study,"" Magn Reson Med, 38(6): 878-883 (1997).
Renshaw, P.F. and Lyoo, I.K., "Creatine augmentation treatment in major depressive disorder sujects," U.S. National Library of Medicine. Available via U.S. National Institutes of Health (2008). http://clinicaltrials.gov/ct2/show/NCT00729755. Accessed Jul. 20, 2010.
Renshaw, P.F., et al., "Multinuclear magnetic resonance spectroscopy studies of brain purines in major depression," Am J Psychiatry, 158(12): 2048-2055 (2001).
Reynolds, C.F., 3rd, et al., "The future of psychiatry as clinical neuroscience," Acad Med, 84(4): 446-450 (2009).
Rezin, G.T., et al., "Mitochondrial dysfunction and psychiatric disorders," Neurochem Res, 34(6): 1021-1029 (2008).
Roitman, S., et al., "Creatine monohydrate in resistant depression: A preliminary study," Bipolar Disord, 9(7): 754-758 (2007).
Sappey-Marinier, D., et al., "Effect of photic stimulation on human visual cortex lactate and phosphates using 1 h and 31 p magnetic resonance spectroscopy," J Cereb Blood Flow Metab, 12(4): 584-592 (1992).
Schlattner, U., et al., "Mitochondrial creatine kinase in human health and disease," Biochimica et Biophysica Acta (BBA)—Molecular Basis of Disease, 1762(2): 164-180 (2006).
Schneeweiss, S., et al., "Comparative safety of antidepressant agents for children and adolescents regarding suicidal acts," Pediatrics, 125(5): 876-888 (2010).
Serene, J.A., et al., "Neuroimaging studies of children with serious emotional disturbances: A selective review," Can J Psychiatry, 52(3): 135-145 (2007).
Shao, L., et al., "Mitochondrial involvement in psychiatric disorders," Arm Med, 40(4): 281-295 (2008).
Shearer, M.C. and Bermingham, S.L., "The ethics of paediatric anti-depressant use: Erring on the side of caution," J Med Ethics, 34(10): 710-714 (2008).
Stork, C. and Renshaw, P.F., "Mitochondrial dysfunction in bipolar disorder: Evidence from magnetic resonance spectroscopy research," Mol Psychiatry, 10(10): 900-919 (2005).
The global burden of disease: 2004 update, vol. 1. 1 edn. WHO Press, World Health Organization, Geneva, Switzerland (2008).
Tsapakis, E.M., et al., "Efficacy of antidepressants in juvenile depression: Meta-analysis," The British Journal of Psychiatry, 193(1): 10-17 (2008).
Usala, T., et al., "Randomised controlled trials of selective serotonin reuptake inhibitors in treating depression in children and adolescents: A systematic review and meta—analysis," European Neuropsychopharmacology, 18(1): 62-73 (2008).
Vitiello, B., et al., "Functioning and quality of life in the treatment for adolescents with depression study (tads)," J Am Acad Child Adolesc Psychiatry, 45(12): 1419-1426 (2006).
Volz, H.P., et al., "31 p magnetic resonance spectroscopy in the frontal lobe of major depressed patients," Eur Arch Psychiatry Clin Neurosci, 248(6): 289-295 (1998).
Wade, T.J., et al., "Emergence of gender differences in depression during adolescence: National panel results from three countries," J Am Acad Child Adolesc Psychiatry, 41(2): 190-198 (2002).
Watanabe, A., et al., ""Effects of creatine on mental fatigue and cerebral hemoglobin oxygenation,"" Neurosci Res, 42(4): 279-285 (2002).
Weissman, M.M., et al., "Depressed adolescents grown up," JAMA, 281(18): 1707-1713 (1999).
Whittington, C.J., et al., "Selective serotonin reuptake inhibitors in childhood depression: Systematic review of published versus unpublished data," Lancet, 363(9418): 1341-1345 (2004).
Wichstrom, L., "The emergence of gender difference in depressed mood during adolescence: The role of intensified gender socialization," Dev Psychol, 35(1): 232-245 (1999).
Wyss, M., et al., "The therapeutic potential of oral creatine supplementation in muscle disease," Med Hypotheses, 51(4): 333-336 (1998).
Zahn-Waxler, C., et al., "Disorders of childhood and adolescence: Gender and psychopathology," Annu Rev Clin Psychol, 4: 275-303 (2008).
International Search Report and Written Opinion was dated Feb. 27, 2012 for Application No. PCT/US11/55399, which was filed on Oct. 7, 2011 and published as WO 2012/048243 on Apr. 12, 2012 (Inventor—Renshaw et al; Applicant—University of Utah) (6 pages).
International Preliminary Report on Patentability was dated Apr. 9, 2013 for Application No. PCT/US11/55399, which was filed on Oct. 7, 2011 and published as WO 2012/048243 on Apr. 12, 2012 (Inventor—Renshaw et al; Applicant—University of Utah) (5 pages).
Preliminary Amendment was dated Apr. 5, 2013 to the U.S. Patent and Trademark Office for U.S. Appl. No. 13/878,191, filed Oct. 7, 2011 and published as US-2013-0324609-A1 on Dec. 5, 2013 (Inventor—Renshaw et al; Applicant—University of Utah) (4 pages).
Preliminary Amendment was dated Jul. 23, 2013 to the U.S. Patent and Trademark Office for U.S. Appl. No. 13/878,191, filed Oct. 7, 2011 and published as US-2013-0324609-A1 on Dec. 5, 2013 (Inventor—Renshaw et al; Applicant—University of Utah) (5 pages).

(56) References Cited

OTHER PUBLICATIONS

Requirement for Restriction/Election was dated Oct. 3, 2014 by the U.S. Patent and Trademark Office for U.S. Appl. No. 13/878,191, filed Oct. 7, 2011 and published as US-2013-0324609-A1 on Dec. 5, 2013 (Inventor—Renshaw et al; Applicant—University of Utah) (9 pages).

Response to Requirement for Restriction/Election was dated Feb. 3, 2015 to the U.S. Patent and Trademark Office for U.S. Appl. No. 13/878.191, filed Oct. 7, 2011 and published as US-2013-0324609-A1 on Dec. 5, 2013 (Inventor—Renshaw et al; Applicant—University of Utah) (8 pages).

Non Final Rejection was dated Apr. 6, 2015 by the U.S. Patent and Trademark Office for U.S. Appl. No. 13/878,191, filed Oct. 7, 2011 and published as US-2013-0324609-A1 on Dec. 5, 2013 (Inventor—Renshaw et al; Applicant—University of Utah) (13 pages).

Reponse to Non Final Rejection was dated Jul. 6, 2015 to the U.S. Patent and Trademark Office for U.S. Appl. No. 13/878,191, filed Oct. 7, 2011 and published as US-2013-0324609-A1 on Dec. 5, 2013 (Inventor—Renshaw et al; Applicant—University of Utah) (12 pages).

Final Rejection was dated Oct. 5, 2015 by the U.S. Patent and Trademark Office for U.S. Appl. No. 13/878,191, filed Oct. 7, 2011 and published as US-2013-0324609-A1 on Dec. 5, 2013 (Inventor—Renshaw et al; Applicant—University of Utah) (13 pages).

Non Final Rejection was dated Jul. 11, 2016 by the U.S. Patent and Trademark Office for U.S. Appl. No. 13/878,191, filed Oct. 7, 2011 and published as US-2013-0324609-A1 on Dec. 5, 2013 (Inventor—Renshaw et al; Applicant—University of Utah) (14 pages).

International Search Report and Written Opinion was dated Apr. 28, 2015 for Application No. PCT/US2015/014856, filed Feb. 6, 2015 and published as WO2015/120299 on Aug. 13, 2015 (Inventor—Renshaw et al; Applicant—University of Utah) (7 pages).

International Preliminary Report on Patentability issued by the International Bureau on Apr. 9, 2013 for PCT/US2011/055399 filed on Oct. 7, 2011 and published as WO 2012/048243 on Apr. 12, 2012 (Inventors—Renshaw et al. // Applicant—University of Utah Research Foundation // (5 pages).

International Search Report and Written Opinion issued by the International Bureau dated Feb. 27, 2012 for PCT/US2011/055399 filed on Oct. 7, 2011 and published as WO 2012/048243 on Apr. 12, 2012 (Inventors—Renshaw et al. // Applicant—University of Utah Research Foundation // (6 pages).

Supplementary European Search Report dated Aug. 30, 2017 by the European Patent Office for Patent Application No. 15746527.9, which was filed on Feb. 6, 2015 and published as EP 3102227 on Dec. 14, 2016 (Inventor—Renshaw et al.; Applicant—University of Utah Research Foundation; (7 pages).

* cited by examiner

COMBINATION OF CREATINE, AN OMEGA-3 FATTY ACID, AND CITICOLINE

CROSS-REFERENCE TO RELATED APPLICATIONS

This Application claims the benefit of and priority under 35 U.S.C. § 371 of PCT/US2015/014856, filed Feb. 6, 2014, which claims the benefit under 35 U.S.C. § 119(e) of U.S. Provisional Patent Application No. 61/937,328, filed on Feb. 7, 2014, which are incorporated herein by reference in entirety.

BACKGROUND

Depression and anxiety disorders are extremely common, with a lifetime prevalence of approximately 17%. These disorders are often chronic and are associated with long duration of episodes and frequent relapses. Indeed, the likelihood of recurrence is greater than 50% (Angst et al., *J. Clin. Psychiatry* 1999, 6, 5). Examples of depression disorders include major depressive disorder, dysthymia, bipolar disorder, seasonal affective disorder, cyclothymia, and postnatal depression. Examples of anxiety disorders include panic disorder, obsessive-compulsive disorder, post-traumatic stress disorder, social anxiety disorder, specific phobias, and generalized anxiety disorder. These disorders are often characterized by both psychosocial and physical impairment, with a high suicide rate among those affected. Because most antidepressants with clinical efficacy act upon monoamines (primarily norepinephrine and serotonin), much research on depression and anxiety has focused upon interactions between these neurotransmitters and their reuptake transporters and receptor proteins.

While the pharmacological action of antidepressants occurs within minutes to hours after administration, the clinical effect and alleviation of symptoms can take up to two weeks following chronic administration. This discrepancy suggests that focusing on monoamine depletion as the underlying pathogenesis of depression may be oversimplified. Several neurotransmitters and neuropeptides are involved in the complex neuroanatomical pathways in anxiety. Intracellular signaling pathways involved in stress-related disorders appear to be intimately associated with the metabolic integrity and capacity of mitochondria to maintain energetic parameters and ultimately cellular stability. Future therapeutic intervention may lie in better understanding this relationship. Treating mitochondrial function may therefore offer a novel avenue for the development of therapies for the treatment of depression- and anxiety-related disorders.

Creatine, omega-3 fatty acids, and citicoline all serve to augment brain mitochondrial function by different mechanisms of action. Creatine plays an essential role in energy metabolism by interconversion of its high-energy phosphorylated analog phosphocreatine, which serves as a short-term buffer to regenerate adenosine triphosphate (Beard et al., *J. Neurochem.* 2010, 115, 297). The omega-3 fatty acids exist at high levels in mitochondrial phospholipids, suggesting that they are essential for the mitochondrial oxidative phosphorylation system to work efficiently (Eckert et al., *Prostaglandins, Leukotrienes, and Essential Fatty Acids* 2013, 88, 105). Citicoline has been shown to directly increase frontal lobe levels of both phosphocreatine and adenosine triphosphate following chronic oral administration (Silveri et al., *NMR in Biomed.* 2008, 21, 1066).

Despite these beneficial effects, the combinatorial effect of all three substances in unison has not been studied previously. Thus, there remains a need for methods and compositions that overcome these deficiencies and that effectively treat depression in humans. These needs and other needs are satisfied by the present invention.

SUMMARY

In accordance with the purpose(s) of the invention, as embodied and broadly described herein, the invention, in one aspect, relates to a neutraceutical composition comprising: a) at least one creatine or creatine analog; b) at least one omega-3 fatty acid; c) citicoline; and d) optionally, a neutraceutically acceptable carrier.

Also disclosed are pharmaceutical compositions comprising: a) at least one creatine or creatine analog; b) at least one omega-3 fatty acid; c) citicoline; and d) optionally, a pharmaceutically acceptable carrier.

Also disclosed are methods comprising administering to a subject at least one creatine or creatine analog in an amount from about 30 wt % to about 60 wt %, at least one omega-3 fatty acid in an amount from about 20 wt % to about 40 wt %, and citicoline in an amount from about 10 wt % to about 40 wt %.

Also disclosed are methods of improving neuropsychological performance in a subject, the method comprising administering to the subject at least one creatine or creatine analog, at least one omega-3 fatty acid, and citicoline; wherein at least one creatine or creatine analog, at least one omega-3 fatty acid, and citicoline are administered in an effective amount.

Also disclosed are methods for reducing the likelihood of depression or anxiety symptoms in a subject, the method comprising administering to the subject at least one creatine or creatine analog, at least one omega-3 fatty acid, and citicoline; wherein at least one creatine or creatine analog, at least one omega-3 fatty acid, and citicoline are administered in an effective amount.

Also disclosed are methods for the treatment of a depression disorder in a subject, the method comprising administering to the subject at least one creatine or creatine analog, at least one omega-3 fatty acid, citicoline, and at least one agent known to treat a depression disorder; wherein at least one creatine or creatine analog, at least one omega-3 fatty acid, and citicoline are administered in an effective amount.

Also disclosed are methods of improving complexion in a subject, the method comprising administering to the subject at least one creatine or creatine analog, at least one omega-3 fatty acid, and citicoline; wherein at least one creatine or creatine analog, at least one omega-3 fatty acid, and citicoline are administered in an effective amount.

Also disclosed are methods for manufacturing a medicament comprising: a) at least one creatine or creatine analog; b) at least one omega-3 fatty acid; c) citicoline; and d) optionally, a pharmaceutically acceptable carrier.

Also disclosed are methods for manufacturing a neutraceutical comprising: a) at least one creatine or creatine analog; b) at least one omega-3 fatty acid; c) citicoline; and d) optionally, a neutraceutically acceptable carrier.

Also disclosed are uses of a neutraceutical composition comprising a) at least one creatine or creatine analog; b) at least one omega-3 fatty acid; c) citicoline; and d) optionally, a neutraceutically acceptable carrier; for use in the manufacture of a neutraceutical for improving neuropsychological performance in a subject.

Also disclosed are uses of a neutraceutical composition comprising a) at least one creatine or creatine analog; b) at least one omega-3 fatty acid; c) citicoline; and d) optionally, a neutraceutically acceptable carrier; for use in the manufacture of a neutraceutical for improving complexion in a subject.

Also disclosed are uses of a neutraceutical composition comprising a) at least one creatine or creatine analog; b) at least one omega-3 fatty acid; c) citicoline; and d) optionally, a pharmaceutically acceptable carrier; for use in the manufacture of a medicament for the treatment of a depression or anxiety disorder.

Also disclosed are kits comprising: a) at least one creatine or creatine analog; b) at least one omega-3 fatty acid; and c) citicoline.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
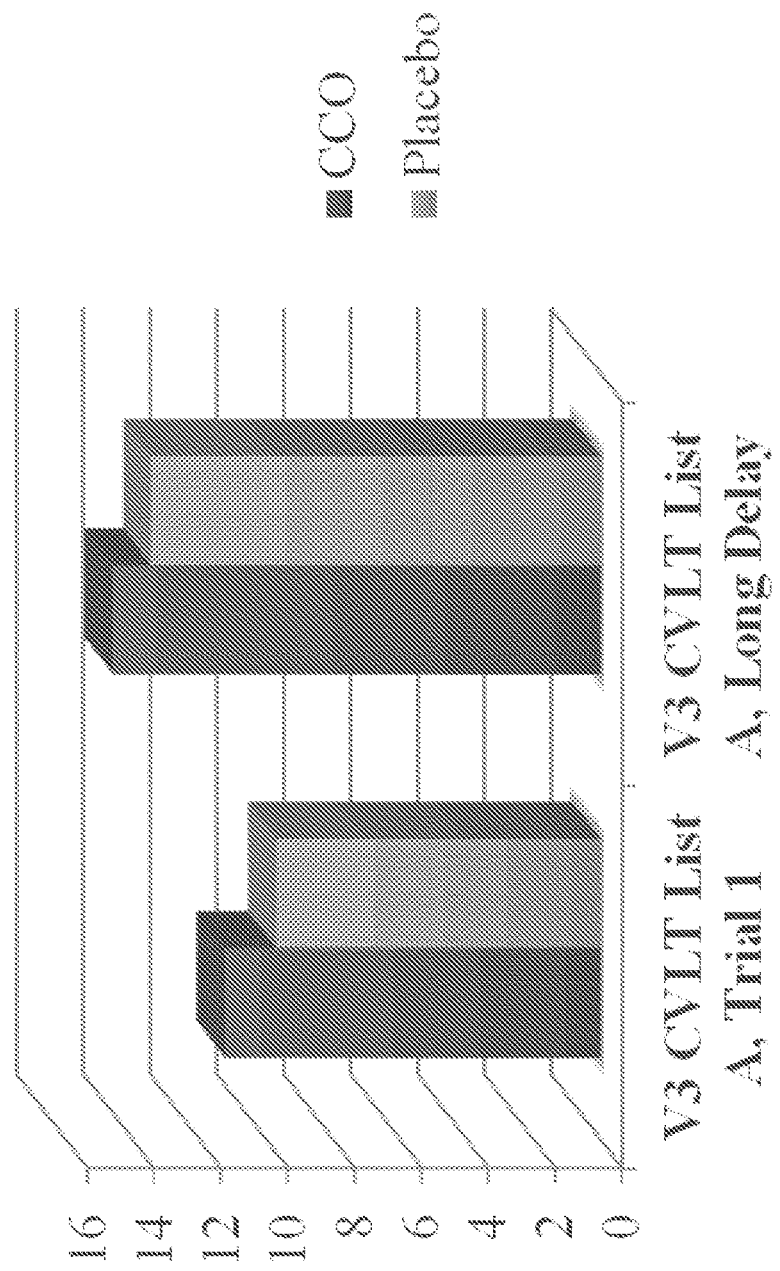
FIG. 1 shows representative data pertaining to the effect of citicoline, creatine, and omega-3 on verbal memory.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples and Figures included herein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated depression disorder prior to the administering step. In some aspects of the disclosed method, the subject has been diagnosed with an increased risk of suicide or suicidal ideation prior to the administering step. In some aspects of the disclosed method, the subject is receiving a therapeutic agent associated with an increased risk of suicide or suicidal ideation prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a clinical interview and/or a physical examination by a person of skill, for example, a physician, and found to have a condition that can be diagnosed or treated by the compounds, compositions, or methods disclosed herein. For example, "diagnosed with a depression disorder" means having been subjected to a clinical interview and/or physical examination by a person of skill, for example, a physician, and found to have a condition that can be diagnosed or treated by a compound or composition that can cure, alleviate, prevent, or otherwise treat a depression disorder.

As used herein, the phrase "identified to be in need of treatment for a disorder," or the like, refers to selection of a subject based upon need for treatment of the disorder. For example, a subject can be identified as having a need for treatment of a disorder (e.g., a disorder related to depression) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

The term "neutraceutically acceptable" describes a material that provides medical or health benefits, including the prevention and treatment of disease. Hence, compositions falling under the label "neutraceutical" may range from isolated nutrients, dietary supplements, and specific diets to genetically engineered designer foods, herbal products, and processed foods such as cereals, soups, and beverages. In various aspects, "neutraceutically acceptable" refers to a material isolated or purified from foods, and generally sold in medicinal forms not usually associated with food, and demonstrated to have a physiological benefit or provide protection against a disease or disorder.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "neutraceutically acceptable carrier" refers to binding agents, fillers, lubricants, disintegrants, or wetting agents. Examples of suitable binding agents, fillers, lubricants, disintegrants, and wetting agents include pregelatinized maize starch, polyvinyl pyrroldiinone, hydroxypropyl methylcellulose, lactose, microcrystalline cellulose, calcium hydrogen phosphate, magnesium stearate, talc, silica, potato starch, sodium starch glycolate, and sodium lauryl sulfate.

The term "stable," as used herein, refers to compounds that are not substantially altered when subjected to conditions to allow for their production, detection, and, in certain aspects, their recovery, purification, and use for one or more of the purposes disclosed herein.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, such as $^{2}$H, $^{3}$H, $^{13}$C, $^{14}$C, $^{15}$N, $^{18}$O, $^{17}$O, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Creatine or Creatine Analogs

In one aspect, the invention relates to creatine or creatine analogs, or pharmaceutically acceptable salts thereof, having a structure represented by a formula:

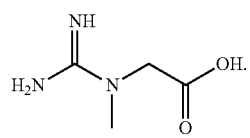

In a further aspect, creatine analogs comprise creatine salts, creatine esters, creatine amides and creatine hydrates. In a still further aspect, creatine esters comprise alkyl esters. In yet a further aspect, creatine esters comprise creatine ethyl ester. In an even further aspect, creatine hydrates comprise creatine monohydrate. In a still further aspect, creatine salts comprise the carboxylate anion form of creatine and a pharmaceutically acceptable cation counterion. In yet a further aspect, creatine salts comprise protonation of the primary amine of creatine with an acid.

In a further aspect, creatine analogs comprise one or more of creatine monohydrate, creatine ethyl ester, creatine citrate, creatine malate, creatine tartrate, and magnesium creatine chelate. In a still further aspect, creatine analogs comprise creatine monohydrate. In yet a further aspect, creatine analogs comprise creatine ethyl ester. In an even further aspect, creatine analogs comprise magnesium creatine chelate. In a still further aspect, creatine analogs comprise creatine monohydrate, creatine ethyl ester and magnesium creatine chelate.

In a further aspect, creatine analogs comprise one or more compounds having a structure of:

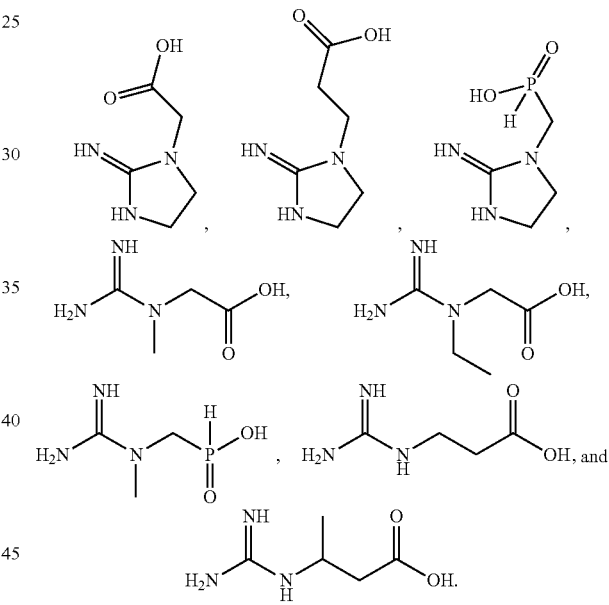

In a further aspect, the creatine analog is a prodrug form of creatine, wherein prodrug is an analog which upon administration to the recipient is capable of providing (directly or indirectly) the compound, or an active metabolite or residue thereof. Such prodrugs are recognizable to those skilled in the art, without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives.

In a further aspect, a prodrug of a creatine analog of the invention is converted within the body, i.e. by hydrolysis in the blood, into its active form that has medical effects. Pharmaceutically acceptable prodrugs are-described in T. Higuchi and V. Stella, Prodrugs as Novel Delivery Systems, Vol. 14 of the A.C.S. Symposium Series, Edward B. Roche, ed.; Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996), 19 (2), 115-130, each of which are incorporated herein by reference.

In a further aspect, prodrugs of a creatine analog of the invention are any covalently bonded carriers that release the compound in vivo when such prodrug is administered to a patient. In a still further aspect, a prodrug is prepared by modifying a functional group in a way such that the modification is cleaved, either by routine manipulation or in vivo, yielding the parent compound. In a still further aspect, a prodrug includes, for example, compounds wherein the amine group is bonded to any group that, when administered to a patient, cleaves to form the amine group. Thus, representative examples of prodrugs include (but are not limited to) acetate, formate, and benzoate derivatives of the amine functional group.

When used herein, the term "alkyl" refers to straight and branched groups containing up to six carbon atoms. Examples of such groups include methyl, ethyl, propyl, isopropyl, n-butyl, isobutyl, tert-butyl, pentyl or hexyl.

When used herein, the term "aryl" refers to, unless otherwise defined, single or fused aromatic rings suitably containing from 4 to 7, preferably 5 or 6, ring atoms in each ring. A fused ring system may include aliphatic rings and need only include one aromatic ring. Examples of suitable aryl rings include phenyl and naphthyl.

When used herein, the term "alkanol" refers to C 1-9 alkyl alcohols, for example methanol, ethanol, industrially methylated spirit (IMS), n-propanol, iso-propanol (IPA), n-butanol, pentanol, hexanol, heptanol, octanol or nonanol, in particular methanol, ethanol, IMS, IPA or n-butanol.

In a further aspect, the creatine or creatine analog is a neutraceutically acceptable derivative. In a still further aspect, the neutraceutically acceptable derivative is a salt, solvate, ester, carbamate, and phosphate ester. In yet a further aspect, "derivative" means any neutraceutically acceptable derivative or non-neutraceutically acceptable derivative which is suitable for use in the process of the present invention. The skilled person will appreciate that non-neutraceutically acceptable derivatives may be used to prepare compounds and derivatives suitable for neutraceutical use.

In a further aspect, creatine or creatine analogs comprise compounds prepared as a neutraceutically acceptable salt. In a still further aspect, a neutraceutically acceptable salt may be readily prepared by using a desired acid or base as appropriate. The salt may precipitate from solution and can be collected by filtration or may be recovered by evaporation of the solvent. In a yet further aspect, salts comprise acid addition salts resulting from reaction of an acid with a basic nitrogen atom.

In a further aspect, the creatine or creatine analog is a pharmaceutically acceptable derivative. In a still further aspect, the pharmaceutically acceptable derivative is a salt, solvate, ester, carbamate, and phosphate ester. In yet a further aspect, "derivative" means any pharmaceutically acceptable derivative or non-pharmaceutically acceptable derivative which is suitable for use in the process of the present invention. The skilled person will appreciate that non-pharmaceutically acceptable derivatives may be used to prepare compounds and derivatives suitable for pharmaceutical use.

In a further aspect, creatine or creatine analogs comprise compounds prepared as a pharmaceutically acceptable salt. For a review on suitable salts see Berge et al., J. Pharm. Sci., 1977, 66, 1-19. In a still further aspect, a pharmaceutically acceptable salt may be readily prepared by using a desired acid or base as appropriate. The salt may precipitate from solution and can be collected by filtration or may be recovered by evaporation of the solvent. In yet a further aspect, salts comprise acid addition salts resulting from reaction of an acid with a basic nitrogen atom.

In a further aspect, a salt within the term "pharmaceutically acceptable salts" refer to non-toxic salts of creatine or creatine analogs of the invention. In a still further aspect, addition salts are formed from acids which form non-toxic salts and comprise acetate, p-aminobenzoate, ascorbate, aspartate, benzenesulfonate, benzoate, bicarbonate, bismethylenesalicylate, bisulfate, bitartrate, borate, bromide, calcium edetate, camsylate, carbonate, chloride, clavulanate, citrate, cyclohexylsulfamate, dihydrochloride, edetate, edisylate, estolate, esylate, ethanedisulfonate, ethanesulfonate, formate, fumarate, gluceptate, gluconate, glutamate, glutarate, glycollate, glycollylarsanilate, hemisulfate, hexylresorcinate, hydrabamine, hydrobromide, hydrochloride, hydrogen phosphate, hydroiodide, hydroxynaphthoate, iodide, isethionate, itaconate, lactate, lactobionate, laurate, malate, maleate, mandelate, mesylate, methylbromide, methylinitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, piruvate, polygalacturonate, propionate, saccharate, salicylate, stearate, subacetate, succinate, sulfate, tannate, tartrate, teoclate, tosylate, triethiodide, trifluoroacetate and valerate. Preferred salts prepared according to the present invention include the succinate, glutarate and hemisulfate salts.

In a further aspect, the invention relates to creatine or creatine analogs, neutraceutically or pharmaceutically acceptable salts thereof having a structure represented by a formula:

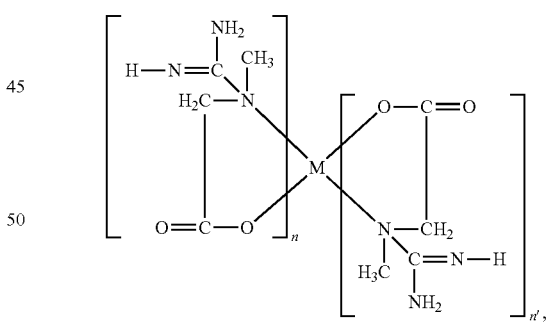

wherein M is a metal, n is 1 and n' is 0, 1, or 2. In a further aspect, n' is 0 providing a ligand to metal molar ratio of 1:1. For example, magnesium creatine may have a ligand to metal molar ratio of 2:1 (n'=1). In a still further aspect, the metal molar ratio is 1:1 (n'=0). In yet a further aspect, ligand to metal molar ratios can be creatine to calcium at 1:1 (n'=0); creatine to zinc at 1:1 (n'=0); creatine to chromium at 1:1 (n'=0), 2:1 (n'=1) and/or 3:1 (n'=2); creatine to manganese at 1:1 (n'=0); and creatine to iron a 1:1 (n'=0), 2:1 (n'=1) and/or 3:1 (n'=2). When n'=0, one or more anions can be present in the solution in a structure represented by a formula:

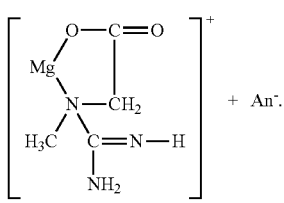

The bonds depicted between the metal (M) and the amine group and between the metal (M) and carboxyl oxygen group as shown and described should not necessarily be strictly construed to represent coordinate covalent bonds. For example, in one aspect, a covalent bond may exists between the metal (M) and the amine group whereas an ionic or coulombic bond exists between the metal (M) and the carboxyl oxygen group in a structure represented by a formula:

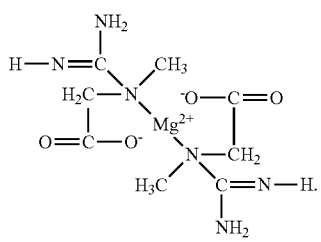

In a further aspect, the net electrical charge at the metal ion is preferably zero. For example, positive charge on the metal ion can be neutralized by electrons contributed by the ligand in formation of the heterocyclic chelate ring.

A method of preparing the creatine chelates of the present invention is as follows. First, a soluble metal salt or an insoluble metal compound is dissolved in water or solubilized in an acidic solution respectively. If an acidic solution is required to disassociate the metal ions, acids such as acetic, citric, lactic, malic, hydrochloric, phosphoric, sulfuric, tartaric, maleic and naturally occurring amino acids such as aminobutyric, aspartic and glutamic acids, etc., may be used. If a metal salt is used that is soluble in water, it may not be required to use an acidic solution, though it may be desired. For example, if magnesium is the metal to be chelated, magnesium sulfate, magnesium citrate, magnesium chloride, magnesium phosphate monobasic, magnesium nitrate, magnesium oxide, etc., may be used as the metal source which will either be dissolved in water or acidified in an acidic solution. To this solution, a creatine ligand is then added. If the pH level is not around neutral, i.e., if it is between about 7.5 and 10, a pH adjuster may be added. pH adjusters may include o-phosphoric acid, citric acid, malic acid, acetic acid, hydrochloric acid, tartaric acid, lactic acid, nitric acid, sulfuric acid and naturally occurring amino acids such as aminobutyric acid, aspartic acid and glutamic acid among others, though o-phosphoric acid is preferred. For example if a creatine chelate is prepared by reacting a creatine ligand with a metal oxide in the presence of citric acid, o-phosphoric acid or another acidifying agent may be added to lower the pH from more basic levels (about 7.5 to 10) to a more neutral pH (about 7).

In a further aspect, the order that one mixes the ingredients is not central to the method of preparing creatine chelates. The creatine ligand can be added to the aqueous acidic solution first, followed by the addition of the metal, or even simultaneously.

In a further aspect, magnesium creatine can be prepared by reacting magnesium oxide, creatine, o-phosphoric acid and citric acid in an aqueous environment. The formulation is stoichiometrically balanced so that no unreacted magnesium oxide remains in the product. Of the possible combinations and permutations, one structure is provided above. In a still further aspect, the ligand to metal molar ratio is 1:1 and the anion may be any of a number of possible corresponding anions such as chloride ($Cl^-$), iodide ($I^-$), bisulfate ($HSO_4^-$), bicarbonate ($HCO_3^-$), dihydrogen phosphate ($H_2PO_4^-$), phosphate ($PO_4^-$), sulfate ($SO_4^{2-}$), citrate, acetate ($C_2H_3O_2^-$), lactate, malate, aminobutyrate, aspartate and glutamate or anions from other soluble salts. In yet a further aspect, the ligand to metal molar ratio is more than 1:1, wherein another creatine anion is present.

In various aspects, the disclosed compositions can comprise at least one creatine or creatine analog in an amount from about 0.05 grams to about 20 grams. In a further aspect, the disclosed compositions can comprise at least one creatine or creatine analog in an amount from about 0.05 grams to about 15 grams. In a still further aspect, the disclosed compositions can comprise at least one creatine or creatine analog in an amount from about 0.05 grams to about 10 grams. In yet a further aspect, the disclosed compositions can comprise at least one creatine or creatine analog in an amount from about 0.05 grams to about 5 grams. In an even further aspect, the disclosed compositions can comprise at least one creatine or creatine analog in an amount from about 0.05 grams to about 1 gram. In a still further aspect, the disclosed compositions can comprise at least one creatine or creatine analog in an amount from about 0.5 grams to about 20 grams. In yet a further aspect, the disclosed compositions can comprise at least one creatine or creatine analog in an amount from about 1 gram to about 20 grams. In an even further aspect, the disclosed compositions can comprise at least one creatine or creatine analog in an amount from about 5 grams to about 20 grams. In a still further aspect, the disclosed compositions can comprise at least one creatine or creatine analog in an amount from about 10 grams to about 20 grams. In yet a further aspect, the disclosed compositions can comprise at least one creatine or creatine analog in an amount from about 15 grams to about 20 grams.

In various aspects, the disclosed compositions can comprise at least about 10 wt % of one or more creatine or creatine analogs. In a further aspect, the disclosed compositions can comprise at least about 20 wt % of one or more creatine or creatine analogs. In a still further aspect, the disclosed compositions can comprise at least about 30 wt % of one or more creatine or creatine analogs. In yet a further aspect, the disclosed compositions can comprise at least about 40 wt % of one or more creatine or creatine analogs. In an even further aspect, the disclosed compositions can comprise at least about 50 wt % of one or more creatine or creatine analogs. In a still further aspect, the disclosed compositions can comprise at least about 60 wt % of one or more creatine or creatine analogs. In yet a further aspect, the disclosed compositions can comprise at least about 70 wt % of one or more creatine or creatine analogs. In an even further aspect, the disclosed compositions can comprise at least about 80 wt % of one or more creatine or creatine analogs.

In a further aspect, the disclosed compositions can comprise one or more creatine or creatine analogs in an amount from about 10 wt % to about 70 wt %. In a still further aspect, the disclosed compositions can comprise one or more creatine or creatine analogs in an amount from about 10 wt % to about 60 wt %. In yet a further aspect, the disclosed compositions can comprise one or more creatine or creatine analogs in an amount from about 10 wt % to about 50 wt %. In an even further aspect, the disclosed compositions can comprise one or more creatine or creatine analogs in an amount from about 10 wt % to about 40 wt %. In a still further aspect, the disclosed compositions can comprise one or more creatine or creatine analogs in an amount from about 20 wt % to about 70 wt %. In yet a further aspect, the disclosed compositions can comprise one or more creatine or creatine analogs in an amount from about 30 wt % to about 70 wt %. In an even further aspect, the disclosed compositions can comprise one or more creatine or creatine analogs in an amount from about 40 wt % to about 70 wt %. In a still further aspect, the disclosed compositions can comprise one or more creatine or creatine analogs in an amount from about 50 wt % to about 70 wt %. In yet a further aspect, the disclosed compositions can comprise one or more creatine or creatine analogs in an amount from about 40 wt % to about 55 wt %.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

C. Omega-3 Fatty Acids

In one aspect, the invention relates to omega-3 fatty acids, or pharmaceutically acceptable salts thereof. An omega-3 fatty acid is an unsaturated fatty acid that contains as its terminus $CH_3$—$CH_2$—$CH$=$CH$—. Generally, an omega-3 fatty acid has the following formula:

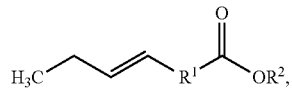

wherein $R^1$ is a C3-C40 alkyl or alkenyl group comprising at least one double bond; and wherein $R^2$ is H or an alkyl group. The term "alkane" or "alkyl" as used herein is a saturated hydrocarbon group (i.e. methyl, ethyl, n-propyl, isopropyl, n-butyl, isobutyl, s-butyl, t-butyl, n-pentyl, iso-pentyl, s-pentyl, neopentyl, hexyl, heptyl, octyl, nonyl, decyl, dodecyl, tetradecyl, hexadecyl, eicosyl, tetracosyl, and the like). The term "alkene" or "alkenyl" as used herein is a hydrocarbon group containing at least one carbon-carbon double bond. Asymmetric structures such as (AB) C=C(CD) are intended to include both the E and Z isomers (cis and trans). In a further aspect, $R^1$ is selected from a C5-C38 alkenyl group, a C6-C36 alkenyl group, a C8-C32 alkenyl group, C12-C30 alkenyl group, C14-C28 alkenyl group, C16-C26 alkenyl group, and a C alkenyl group. In a still further aspect, the alkenyl group of $R^1$ can have from 2 to 6, from 3 to 6, from 4 to 6, or from 5 to 6 double bonds. In yet a further aspect, the alkenyl group of $R^1$ can have from 1, 2, 3, 4, 5, or 6 double bonds, wherein any of the stated values can form an upper or lower endpoint as appropriate.

In various aspects, the at least one omega-3 fatty acid is selected from linolenic acid (18:3ω3) (ALA), octadecatet-raenoic acid (18:4ω3), eicosapentaenoic acid (20:5ω3) (EPA), docosahexaenoic acid (22:6ω3) (DHA), docosapen-taenoic acid (22:6ω3) (DPA). In a further aspect, the at least one omega-3 fatty acid is EPA. Other specific examples include docosahexaenoic acid and/or eicosapentaenoic acid, a C1-C6 alkyl ester thereof, a triglyceride ester thereof, a phytosterol ester thereof, and/or a mixture thereof.

In various aspects, the disclosed compositions comprise at least one salt of a fatty acid, e.g., omega-3 fatty acid. These salts can be, for example, calcium, magnesium, sodium, potassium, or zinc salts, including mixtures thereof. The term "salt" as used herein refers to the acyloxyl group RCOO— and its associated counterion(s) (e.g., Ca, Mg, Na, K, or Zn). The term "salt" is not meant to imply any particular stoichiometric relationship between the acyloxyl group(s) and the counterion(s), which can vary depending on such factors as the amount of hydration, the type of counterion, the valance and size of the counterion, the presence of other compounds, and the like.

In various aspects, the disclosed compositions comprise at least one omega-3 fatty acid residue. The term "residue" as used herein refers to the moiety that is the resulting product of the specified chemical species in a particular reaction scheme or subsequent formulation or chemical product, regardless of whether the moiety is actually obtained from the specified chemical species. For example, an "omega-3 fatty acid residue" refers to the moiety which results when an omega-3 fatty acid participates in a particular reaction (e.g., the residue can be a fatty acyl group RCO— or acyloxyl group RCOO—, where R is the hydrocarbon chain of the omega-3 fatty acid). In this case, the omega-3 fatty acid residue is "derived" from the omega-3 fatty acid. It is understood that this moiety can be obtained by reaction with a species other than the specified omega-3 fatty acid, for example, by reaction with an omega-3 fatty acid chloride, ester, or anhydride. Thus, when a composition is said to have a particular fatty acid residue, the residue can have the formula $RCO_2X$, where R is the hydrocarbon chain and X can be a hydrogen (i.e., the residue is a free, protonated fatty acid), alkyl group (e.g., the residue is a fatty acid ester or triglyceride), or cation (i.e., the residue is a fatty acid salt).

In various aspects, the disclosed compositions can comprise at least one omega-3 fatty acid in an amount from about 0.05 grams to about 10 grams. In a further aspect, the disclosed compositions can comprise at least one omega-3 fatty acid in an amount from about 0.05 grams to about 5 grams. In yet a further aspect, the disclosed compositions can comprise at least one omega-3 fatty acid in an amount from about 0.05 grams to about 1 gram. In an even further aspect, the disclosed compositions can comprise at least one omega-3 fatty acid in an amount from about 0.5 grams to about 10 grams. In a still further aspect, the disclosed compositions can comprise at least one omega-3 fatty acid in an amount from about 1 gram to about 10 grams. In yet a further aspect, the disclosed compositions can comprise at least one omega-3 fatty acid in an amount from about 5 grams to about 10 grams.

In various aspects, the disclosed compositions can comprise at least about 10 wt % of one or more omega-3 fatty acid. In a further aspect, the disclosed compositions can comprise at least about 20 wt % of one or more omega-3 fatty acid. In a still further aspect, the disclosed compositions can comprise at least about 30 wt % of one or more omega-3 fatty acid.

In a further aspect, the disclosed compositions can comprise one or more omega-3 fatty acid in an amount from about 10 wt % to about 50 wt %. In a still further aspect, the disclosed compositions can comprise one or more omega-3 fatty acid in an amount from about 10 wt % to about 40 wt %. In yet a further aspect, the disclosed compositions can comprise one or more omega-3 fatty acid in an amount from about 10 wt % to about 30 wt %. In an even further aspect, the disclosed compositions can comprise one or more omega-3 fatty acid in an amount from about 20 wt % to about 50 wt %. In a still further aspect, the disclosed compositions can comprise one or more omega-3 fatty acid in an amount from about 30 wt % to about 50 wt %. In yet a further aspect, the disclosed compositions can comprise one or more omega-3 fatty acid in an amount from about 30 wt % to about 40 wt %.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

D. Citicoline

In one aspect, the invention relates to citicoline (e.g., cytidine-5'-diphosphocholine or CDP-choline), or pharmaceutically acceptable salts thereof, having a structure represented by a formula:

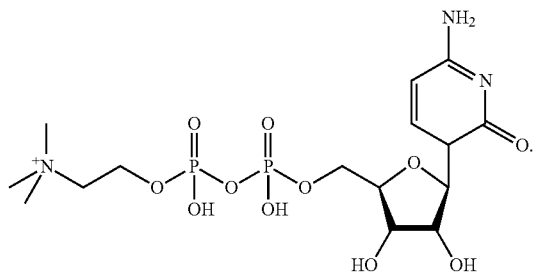

Citicoline is a natural precursor of phosphatidylcholine, which is central to the dynamic regulation of cellular integrity. Citicoline donates the components choline, cytidine, and uridine (precursors to the synthesis of phosphatidylcholine), required to form, repair, and even restore function to nerve cell membranes. Cytidine and uridine, acting through cytidyl triphosphate (CTP), are also involved in the synthesis of other phospholipids. Additionally, choline promotes the synthesis of acetylcholine, a neurotransmitter intimately associated with cognition. As an information-transmitting molecule, acetylcholine is necessary for proper memory function, and is especially important for aging brains. In addition to promoting phospholipid synthesis, citicoline also inhibits phospholipid degradation in the brain. Citicoline's mechanism of action is thought to entail cerebrovascular (blood circulation of the brain) regulation and neuroimmune (immune function of the nervous system) actions in the brain.

Citicoline has demonstrated beneficial effects towards the enhancement of learning and memory in both animal and human studies. Improvements in cognition have also been observed in Alzheimer's disease, Parkinson's disease, dementia, cerebral ischemia, and stroke. In addition, an increasing amount of research has indicated that citicoline administration may benefit a variety of other conditions associated with symptoms of neurological dysfunction including, traumatic head injuries, amblyopia, ischemic optic neuropathy, glaucoma, substance abuse, and appetite control.

In various aspects, the disclosed compositions comprise citicoline in the form of a citicoline-based compound. In a further aspect, the disclosed compositions comprise citicoline in the form of a citicoline precursor. In a still further aspect, the disclosed compositions comprise citicoline in the form of a citicoline salt. In yet a further aspect, the disclosed compositions comprise citicoline in the form of a citicoline source. The citicoline source can include, for example, a citicoline-rich food or dietary product.

In various aspects, the disclosed compositions can comprise at least one citicoline in an amount from about 0.05 grams to about 10 grams. In a further aspect, the disclosed compositions can comprise at least citicoline in an amount from about 0.05 grams to about 5 grams. In yet a further aspect, the disclosed compositions can comprise at least one citicoline in an amount from about 0.05 grams to about 1 gram. In an even further aspect, the disclosed compositions can comprise at least one citicoline in an amount from about 0.5 grams to about 10 grams. In a still further aspect, the disclosed compositions can comprise at least one citicoline in an amount from about 1 gram to about 10 grams. In yet a further aspect, the disclosed compositions can comprise at least one citicoline in an amount from about 5 grams to about 10 grams.

In various aspects, the disclosed compositions can comprise at least about 5 wt % of citicoline. In a further aspect, the disclosed compositions can comprise at least about 10 wt % of citicoline. In a still further aspect, the disclosed compositions can comprise at least about 15 wt % of citicoline. In yet a further aspect, the disclosed compositions can comprise at least about 20 wt % of citicoline. In an even further aspect, the disclosed compositions can comprise at least about 25 wt % of citicoline. In a still further aspect, the disclosed compositions can comprise at least about 30 wt % of citicoline. In yet a further aspect, the disclosed compositions can comprise at least about 35 wt % of citicoline.

In a further aspect, the disclosed compositions can comprise citicoline in an amount from about 5 wt % to about 50 wt %. In a still further aspect, the disclosed compositions can comprise citicoline in an amount from about 5 wt % to about 40 wt %. In yet a further aspect, the disclosed compositions can comprise citicoline in an amount from about 5 wt % to about 30 wt %. In an even further aspect, the disclosed compositions can comprise citicoline in an amount from about 5 wt % to about 20 wt %. In a still further aspect, the disclosed compositions can comprise citicoline in an amount from about 15 wt % to about 50 wt %. In yet a further aspect, the disclosed compositions can comprise citicoline in an amount from about 20 wt % to about 50 wt %. In an even further aspect, the disclosed compositions can comprise citicoline in an amount from about 25 wt % to about 50 wt %. In a still further aspect, the disclosed compositions can comprise citicoline in an amount from about 30 wt % to about 50 wt %. In yet a further aspect, the disclosed compositions can comprise citicoline in an amount from about 10 wt % to about 20 wt %.

E. Neitraceutical Compositions

In one aspect, the invention relates to neutraceutical compositions comprising: a) at least one creatine or creatine analog; b) at least one omega-3 fatty acid; c) citicoline; and d) optionally, a neutraceutically acceptable carrier, wherein at least one creatine or creatine analog, at least one omega-3 fatty acid, and citicoline are together present in a neutraceutically effective amount. In a further aspect, at least one of the creatine or creatine analog, the omega-3 fatty acid, or citicoline is present in an individually neutraceutically effective amount. That is, a neutraceutical composition can be provided comprising a neutraceutically effective amount of at least one creatine or creatine analog, at least one omega-3 fatty acid, and citicoline, or at least one product of a disclosed method and a neutraceutically acceptable carrier.

In certain aspects, the disclosed neutraceutical compositions comprise the disclosed compounds and pharmaceutically acceptable salt(s) thereof as an active ingredient, a neutraceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the condition(s) for which the active ingredient is being administered. The neutraceutical compositions can be conveniently presented in unit dosage form and prepared by any of the methods well known in the art.

As used herein, the term "neutraceutically acceptable salts" refers to salts prepared from neutraceutically acceptable non-toxic bases or acids. When the compound of the present invention is acidic, its corresponding salt can be conveniently prepared from neutraceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from neutraceutically acceptable organic non-toxic bases include salts of primary, secondary, and tertiary amines, as well as cyclic amines and substituted amines such as naturally occurring and synthesized substituted amines. Other neutraceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "neutraceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or neutraceutically acceptable salts thereof, of this invention can be combined as the active ingredient in intimate admixture with a neutraceutical carrier according to conventional neutraceutical compounding techniques. The carrier can take a wide variety of forms depending on the form of preparation desired for administration, e.g., oral or parenteral (including intravenous). Thus, the neutraceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or neutraceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the neutraceutical compositions of this invention can include a neutraceutically acceptable carrier and a compound or a neutraceutically acceptable salt of the compounds of the invention. The compounds of the invention, or neutraceutically acceptable salts thereof, can also be included in neutraceutical compositions in combination with one or more other therapeutically active compounds.

The neutraceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient neutraceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid neutraceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The neutraceutical compositions of the present invention comprise at least one creatine or creatine analog, at least one omega-3 fatty aced, and citicoline (or neutraceutically acceptable salts thereof) as active ingredients, and optionally, a neutraceutically acceptable carrier. The instant compositions include compositions suitable for oral, rectal, topical, and parenteral (including subcutaneous, intramuscular, and intravenous) administration, although the most suitable route in any given case will depend on the particular host, and nature and severity of the condition(s) for which the active ingredient is being administered. The neutraceutical compositions can be conveniently presented in unit dosage form and prepared by any of the methods well known in the art.

Neutraceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or neutraceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In addition to the aforementioned carrier ingredients, the neutraceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the at least one creatine or creatine analog is present in an amount from about 30 wt % to about 60 wt % of the composition. In a still further aspect, the at least one creatine or creatine analog is selected from creatine, creatine monohydrate, creatine ethyl ester, creatine citrate, creatine malate, creatine tartrate, and magnesium creatine chelatem, or a mixture thereof. In yet a further aspect, the at least one creatine or creatine analog comprises a precursor of s-adenosyl methionine. In an even further aspect, the precursor is a direct precursor. In a still further aspect, the direct precursor is guanidinoacetate. In an even further aspect, the at least one creatine or creatine analog comprises s-adenosyl methionine.

In a further aspect, the at least one omega-3 fatty acid is present in an amount from about 20 wt % to about 40 wt % of the composition. In a still further aspect, the at least one omega-3 fatty acid is selected from $\alpha$-linolenic acid (ALA), eicosapentaenoic acid (EPA), and docosahexaenoic acid (DHA), or a mixture thereof. In yet a further aspect, the at least one omega-3 fatty acid is EPA.

In a further aspect, the citicoline is present in an amount from about 10 wt % to about 40 wt % of the composition.

In a further aspect, the composition is formulated for oral administration.

The disclosed neutraceutical compositions can further comprise other neutraceutically active compounds, which are usually applied in the treatment of the above mentioned pathological condition(s).

It is understood that the disclosed compositions can be prepared from the disclosed compounds. It is also understood that the disclosed compositions can be employed in the disclosed methods of using.

F. Pharmaceutical Compositions

In one aspect, the invention relates to pharmaceutical compositions comprising: a) at least one creatine or creatine analog; b) at least one omega-3 fatty acid; c) citicoline; and e) optionally, a pharmaceutically acceptable carrier, wherein the at least one creatine or creatine analog, the at least one omega-3 fatty acid, and citicoline are together present in a therapeutically effective amount. In a further aspect, at least one of the creatine or creatine analog, the omega-3 fatty acid, or citicoline is present in an individually therapeutically effective amount. That is, a pharmaceutical composition can be provided comprising a therapeutically effective amount of at least one creatine or creatine analog, at least one omega-3 fatty acid, and citicoline or at least one product of a disclosed method and a pharmaceutically acceptable carrier.

In certain aspects, the disclosed pharmaceutical compositions comprise the disclosed compounds and pharmaceutically acceptable salt(s) thereof as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise at least one creatine or creatine analog, at least one omega-3 fatty acid, and citicoline (or pharmaceutically acceptable salts thereof) as active ingredients, and optionally, a pharmaceutically acceptable carrier. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carriers) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the at least one of the creatine or creatine analog, the omega-3 fatty acid, or citicoline of the composition is present in a therapeutically effective amount.

In a further aspect, the at least one creatine or creatine analog is present in an amount from about 30 wt % to about 60 wt % of the composition. In a still further aspect, the at least one creatine or creatine analog is selected from creatine monohydrate, creatine ethyl ester, creatine citrate, creatine malate, creatine tartrate, and magnesium creatine chelatem, or a mixture thereof. In yet a further aspect, the at least one creatine or creatine analog comprises a precursor of s-adenosyl methionine. In an even further aspect, the precursor is a direct precursor. In a still further aspect, the direct precursor is guanidinoacetate. In an even further aspect, the at least one creatine or creatine analog comprises s-adenosyl methionine.

In a further aspect, the at least one omega-3 fatty acid is present in an amount from about 20 wt % to about 40 wt % of the composition. In a still further aspect, the at least one omega-3 fatty acid is selected from a-linolenic acid (ALA), eicosapentaenoic acid (EPA), and docosahexaenoic acid (DHA), or a mixture thereof. In yet a further aspect, the at least one omega-3 fatty acid is EPA.

In a further aspect, the citicoline is present in an amount from about 10 wt % to about 40 wt % of the composition.

In a further aspect, the composition is formulated for oral administration.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

G. Methods of Administering the Compounds and Compositions

In one aspect, the invention relates to a method comprising administering to a subject at least one creatine or creatine analog in an amount from about 30 wt % to about 60 wt %, at least one omega-3 fatty acid in an amount from about 20 wt % to about 40 wt %, and citicoline in an amount from about 10 wt % to about 40 wt %.

In a further aspect, the at least one or creatine or creatine analogs of the method is present in an amount from about 10 wt % to about 70 wt %. In a still further aspect, the at least one or creatine or creatine analogs is present in an amount from about 10 wt % to about 60 wt %. In yet a further aspect, the at least one or creatine or creatine analogs is present in an amount from about 10 wt % to about 50 wt %. In an even further aspect, the at least one or creatine or creatine analogs is present in an amount from about 10 wt % to about 40 wt %. In a still further aspect, the at least one or creatine or creatine analogs is present in an amount from about 20 wt % to about 70 wt %. In yet a further aspect, the at least one or creatine or creatine analogs is present in an amount from about 30 wt % to about 70 wt %. In an even further aspect, the at least one or creatine or creatine analogs is present in an amount from about 40 wt % to about 70 wt %. In a still further aspect, the at least one or creatine or creatine analogs is present in an amount from about 50 wt % to about 70 wt %.

In a further aspect, the at least one omega-3 fatty acid of the method is present in an amount from about 10 wt % to about 50 wt %. In a still further aspect, the at least one omega-3 fatty acid is present in an amount from about 10 wt % to about 40 wt %. In yet a further aspect, the at least one omega-3 fatty acid is present in an amount from about 10 wt % to about 30 wt %. In an even further aspect, the at least one omega-3 fatty acid is present in an amount from about 20 wt % to about 50 wt %. In a still further aspect, the at least one omega-3 fatty acid is present in an amount from about 30 wt % to about 50 wt %.

In a further aspect, the citicoline of the method is present in an amount from about 5 wt % to about 50 wt %. In a still further aspect, the citicoline is present in an amount from about 5 wt % to about 40 wt %. In yet a further aspect, the citicoline is present in an amount from about 5 wt % to about 30 wt %. In an even further aspect, the citicoline is present in an amount from about 5 wt % to about 20 wt %. In a still further aspect, the citicoline is present in an amount from about 15 wt % to about 50 wt %. In yet a further aspect, the citicoline is present in an amount from about 20 wt % to about 50 wt %. In an even further aspect, the citicoline is present in an amount from about 25 wt % to about 50 wt %. In a still further aspect, the citicoline is present in an amount from about 30 wt % to about 50 wt %.

In a further aspect, the at least one creatine or creatine analog, at least one omega-3 fatty acid, and citicoline are co-packaged. In a still further aspect, the at least one creatine or creatine analog, at least one omega-3 fatty acid, and citicoline are co-formulated. In yet a further aspect, the at least one creatine or creatine analog and at least one omega-3 fatty acid are co-packaged. In an even further aspect, the at least one creatine or creatine analog and at least one omega-3 fatty acid are co-formulated. In a still further aspect, the at least one creatine or creatine analog and citicoline are co-packaged. In yet a further aspect, the at least one creatine or creatine analog and citicoline are co-formulated. In an even further aspect, the at least one omega-3 fatty acid and citicoline are co-packaged. In a still further aspect, the at least one omega-3 fatty acid and citicoline are co-formulated.

In a further aspect, the at least one creatine or creatine analog, at least one omega-3 fatty acid, and citicoline are administered within a 24 h time period.

H. Methods of Using the Compounds and Compositions

The disclosed compounds can be used as single agents or in combination with one or more other drugs in the treatment, prevention, control, amelioration or reduction of risk of the aforementioned diseases, disorders and conditions for which the disclosed compounds or the other drugs have utility, where the combination of drugs together are safer or more effective than either drug alone. The other drug(s) can be administered by a route and in an amount commonly used therefore, contemporaneously or sequentially with a disclosed compound. When the disclosed compounds are used contemporaneously with one or more other drugs, a pharmaceutical or neutraceutical composition in unit dosage form containing such drugs and the disclosed compounds is preferred. However, the combination therapy can also be administered on overlapping schedules. It is also envisioned that the combination of one or more active ingredients and the disclosed compounds will be more efficacious than either as a single agent.

The neutraceutical compositions and methods of the present invention can further comprise other neutraceutically active compounds as noted herein which are usually applied in the treatment of the above mentioned pathological conditions.

The pharmaceutical compositions and methods of the present invention can further comprise other therapeutically active compounds as noted herein which are usually applied in the treatment of the above mentioned pathological conditions.

1. Reducing Likelihood of Depression or Anxiety Symptoms

In one aspect, the invention relates to a method of reducing the likelihood of depression or anxiety symptoms in a subject, the method comprising administering to the subject at least one creatine or creatine analog, at least one omega-3 fatty acid, and citicoline; wherein at least one creatine or creatine analog, at least one omega-3 fatty acid, and citicoline are together administered in an effective amount. In a further aspect, the at least one of the creatine or creatine analog, the at least one omega-3 fatty acid, or citicoline is individually administered in an effective amount.

In a further aspect, the subject has been diagnosed with a depression or anxiety disorder prior to the administering step. In a still further aspect, the subject has been treated for a depression or anxiety disorder prior to the administering step. In yet a further aspect, the method further comprises the step of identifying a subject in need of treatment of a depression or anxiety disorder.

In a further aspect, the effective amount is a neutraceutically effective amount. In a still further aspect, the effective amount is a therapeutically effective amount.

In a further aspect, the at least one creatine or creatine analog, at least one omega-3 fatty acid, and citicoline are administered within ten days of administration to the subject an agent known to have a side effect of causing depression or anxiety.

In a further aspect, the agent known to have a side effect of increasing the likelihood of depression or anxiety symptoms is selected from an anticonvulsant, a barbiturate, a benzodiazepine, a β-adrenergic blocker, a calcium channel blocker, an estrogen, a fluoroquinolone, an interferon alpha, an opiod, and a statin. In a still further aspect, the agent known to have a side effect of increasing the likelihood of depression or anxiety symptoms is selected from Abilify® (aripiprazole), Accutane® (isotretinoin), Ambien® (Zolpidem), Antabuse® (disulfiram), Chantix® (varenicline), Lariam® (mefloquine), Norplant® (levonorgestrel Implant), Parlodel® (bromocriptine), Savella® (milnacipran), Singulair® (montelukast), Strattera® (atomoxetine), tetrabenazine, tramadol, and Zovirax® (acyclovir).

2. Treatment of a Depression Disorder

In one aspect, the invention relates to a method for the treatment of a depression disorder in a subject, the method comprising administering to the subject at least one creatine or creatine analog, at least one omega-3 fatty acid, citicoline, and at least one agent known to treat a depression disorder; wherein at least one creatine or creatine analog, at least one omega-3 fatty acid, and citicoline are together administered in an effective amount. In a further aspect, at least one of the creatine or creatine analog, the omega-3 fatty acid, or citicoline is individually administered in an effective amount.

In a further aspect, the method further comprises the step of identifying a subject in need of treatment of a depression disorder.

a. Depression Disorders

In various aspects, the depression disorder is selected from major depressive disorder, minor depression disorder, dysthymia, postpartum depression, seasonal affective disorder, bipolar disorder, mixed anxiety depression, unspecified depression, adjustment disorder, atypical depression, psychotic depression, and suicidal ideation. In a further aspect, the depression disorder is major depressive disorder.

In various aspects, the agent known to treat a depression disorder is selected from selective serotonin reuptake inhibitor, serotonin-norepinephrine reuptake inhibitors, tricyclic antidepressants, tetracyclic antidepressants, phenylpiperazine antidepressants, monoamine oxidase inhibitors, and atypical antidepressants. In a further aspect, the agent known to treat a depression disorder is selected from fluoxetine, escitalopram, citalopram, paroxetine, fluvoxamine, sertraline, venlafaxine, desvenlafaxine, duloxetine, milnacipran, amoxapine, imipramine, trimipramine, nortriptyline, clomipramine, amitriptyline, doxepin, protriptyline, desipramine, tranylcypromine, isocarboxazid, selegiline, and phenelzine.

b. Dosages

Typically, at least one creatine or a creatine analog, at least one omega-3 fatty acid, and citicoline are administered to a subject; wherein at least one creatine or creatine analog, at least one omega-3 fatty acid, and citicoline are together administered in an effective amount. In a further aspect, at least one of the creatine or creatine analog, the omega-3 fatty acid, or citicoline is individually administered in an effective amount.

In a further aspect, the effective amount is a therapeutically effective amount. In a still further aspect, the effective amount is a neutraceutically effective amount. In yet a further aspect, the effective amount is a prophylactically effective amount. In an even further aspect, the effective amount is a synergistically effective amount.

In a further aspect, the at least one or creatine or creatine analogs of the method is administered in an amount from about 10 wt % to about 70 wt % of the composition. In a still further aspect, the at least one or creatine or creatine analogs is administered in an amount from about 10 wt % to about 60 wt % of the composition. In yet a further aspect, the at least one or creatine or creatine analogs is administered in an amount from about 10 wt % to about 50 wt % of the composition. In an even further aspect, the at least one or creatine or creatine analogs is administered in an amount from about 10 wt % to about 40 wt % of the composition. In a still further aspect, the at least one or creatine or creatine analogs is administered in an amount from about 20 wt % to about 70 wt % of the composition. In yet a further aspect, the at least one or creatine or creatine analogs is administered in an amount from about 30 wt % to about 70 wt % of the composition. In an even further aspect, the at least one or creatine or creatine analogs is administered in an amount from about 40 wt % to about 70 wt % of the composition. In a still further aspect, the at least one or creatine or creatine analogs is administered in an amount from about 50 wt % to about 70 wt % of the composition.

In a further aspect, the at least one omega-3 fatty acid of the method is administered in an amount from about 10 wt % to about 50 wt % of the composition. In a still further aspect, the at least one omega-3 fatty acid is administered in an amount from about 10 wt % to about 40 wt % of the composition. In yet a further aspect, the at least one omega-3 fatty acid is administered in an amount from about 10 wt % to about 30 wt % of the composition. In an even further aspect, the at least one omega-3 fatty acid is administered in an amount from about 20 wt % to about 50 wt % of the composition. In a still further aspect, the at least one omega-3 fatty acid is administered in an amount from about 30 wt % to about 50 wt % of the composition.

In a further aspect, the citicoline of the method is administered in an amount from about 5 wt % to about 50 wt % of the composition. In a still further aspect, the citicoline is administered in an amount from about 5 wt % to about 40 wt % of the composition. In yet a further aspect, the citicoline is administered in an amount from about 5 wt % to about 30 wt % of the composition. In an even further aspect, the citicoline is administered in an amount from about 5 wt % to about 20 wt % of the composition. In a still further aspect, the citicoline is administered in an amount from about 15 wt % to about 50 wt % of the composition. In yet a further aspect, the citicoline is administered in an amount from about 20 wt % to about 50 wt % of the composition. In an even further aspect, the citicoline is administered in an amount from about 25 wt % to about 50 wt % of the composition. In a still further aspect, the citicoline is administered in an amount from about 30 wt % to about 50 wt % of the composition.

In a further aspect, the at least one creatine or creatine analog, at least one omega-3 fatty acid, and citicoline are co-packaged. In a still further aspect, the at least one creatine or creatine analog, at least one omega-3 fatty acid, and citicoline are co-formulated. In yet a further aspect, the at least one creatine or creatine analog and at least one omega-3 fatty acid are co-packaged. In an even further aspect, the at least one creatine or creatine analog and at least one omega-3 fatty acid are co-formulated. In a still further aspect, the at least one creatine or creatine analog and citicoline are co-packaged. In yet a further aspect, the at least one creatine or creatine analog and citicoline are co-formulated. In an even further aspect, the at least one omega-3 fatty acid and citicoline are co-packaged. In a still further aspect, the at least one omega-3 fatty acid and citicoline are co-formulated.

In one aspect, the amount can be given once per day. In a further aspect, half of the amount can be given twice per day. In a further aspect, one-third of the amount can be given three times per day.

c. Diagnosis of a Depression Disorder

In various aspects, a diagnosis of a depression disorder comprises determining, in a brain of a patient, levels of a marker (e.g., a metabolite) indicative of a brain bioenergetic metabolic state of the patient, the brain bioenergetic metabolic state being predictive as to whether the patient will manifest reduced symptoms of depression in response to a depression treatment. In a further aspect, the marker is detected in a region of the brain comprising at least one of the anterior cingulate, the amygdala, and the hippocampus of the brain.

In various aspects, diagnosed comprises performing a $^{31}P$ MRS experiment upon the subject and identifying a level of a metabolic marker. In a further aspect, the marker comprises at least one of adenosine triphosphate, adenosine diphosphate, and phosphocreatine. In a still further aspect, the first and second levels of the marker are determined by $^{31}P$ magnetic resonance spectroscopy or MR spectroscopy of another suitable isotope. In yet a further aspect, the marker comprises at least one of brain tissue magnesium concentration, intracellular pH level, total brain tissue nucleoside concentration, brain tissue phosphocreatine concentration, and brain tissue β nucleoside triphosphate concentration. In an even further aspect, the marker can also be any other known to those of skill in the art. In an even further aspect, the marker comprises phosphocreatine.

In various aspects, the marker comprises a brain bioenergetic metabolic state marker, wherein the brain energetic metabolic state marker comprises a pH, a compound comprising magnesium, and a compound comprising phosphorus (e.g., PCr, ATP, ADP, $P_i$, total NTP, α-NTP, β-NTP, γ-NTP, and combinations thereof). As used herein, "PCr" means phosphocreatine. In a further aspect, levels of such phosphorus comprising compounds present in the brain of a patient can be determined by, for instance, $^{31}P$ MRS. In a still further aspect, the patient can suffer from major depression disorder. In a further aspect, the patient can suffer from depression resulting from recurring head pain, such as migraine headaches, cluster headaches, and tension headaches. In a still further aspect, the antidepression treatment can comprise administering to the patient a SSRI, a tricyclic, a thyroid hormone, or combinations thereof.

In various aspects, brain levels of ADP, ATP, and PCr are different, as compared to a subject that does not suffer from depression, in the brain of a subject that suffers from depression and that will likely manifest reduced levels and/or symptoms of depression in response to an antidepression treatment. In some embodiments, an antidepression treatment results in a substantial normalization of brain levels of ADP, ATP, and PCr in the brain of a patient that manifests reduced levels and/or symptoms of depression in response to the antidepression treatment. In a further aspect, normalizing changes in brain PCr and ATP levels in can result in the achievement of a substantially normalized brain bioenergetic metabolic state as a result of the buffer role of PCr in relation to ATP. For example, brain concentrations of ATP can, at the expense of brain PCr concentrations, normally be maintained at substantially uniform levels by PCr transfer of a high-energy phosphate group to ADP, reforming ATP in a reaction mediated by, for example, creatine kinase. A reduction of an brain concentration of ADP, ATP, or PCr to a substantially non-physiologic level can result in a brain metabolic state correlated with depression. An antidepression treatment that substantially normalizes a level of ADP, ATP, or PCr in a patient suffering from depression can thereby alleviate a level or symptom of depression in the patient. But such normalizing changes in brain ADP, ATP, and PCr brain concentrations in patients that respond to a depression treatment can also be achieved by other mechanisms.

In various aspects, a mitochondrial dysfunction characterizes a patient that manifests reduced levels and/or symptoms of depression in response to an antidepression treatment modality. In a further aspect, low levels of magnesium in the brain of a subject that suffers from depression, as compared with normal subjects, can result from impaired oxidative phosphorylation related to mitochondrial dysfunction; and impaired oxidative phosphorylation can result in a brain bioenergetic metabolic state correlated with depression. An antidepression treatment that substantially normalizes, in a patient suffering from depression, brain magnesium levels resulting from mitochondrial dysfunction can alleviate a level or symptom of depression in the patient. But such normalizing changes in levels of magnesium in the brain of a patient that responds to a depression treatment modality can also be achieved by other mechanisms.

In various aspects, a diagnosis of a depression disorder comprises a medical history. In a further aspect, symptoms of depression can include, for example, depressive mood, hypobulia, loss of interest and pleasure, disrupted concentration and attention, lowered self-esteem and self-confidence, feelings of guilt and worthlessness, pessimism about the future, thoughts of suicide, sleep disorders, and loss of appetite. These symptoms have features peculiar to depression, which differ from depressed feelings experienced by anyone, and also differ from the lowered mental activity and sense of exhaustion experienced by people afflicted with physical diseases. The symptoms of depression are mainly comprehended by taking a precise medical history, questioning when and how the symptoms in terms of mental activity were developed and what types of damages have been imposed upon their social and domestic lives, and confirming various symptoms based on a patient's attitude or the contents of conversations during consultation. For example, family medical history, anamnesis, physical conditions, early developmental history, life history, personality inclination, premorbid social adaptation, and the occurrence of any episode(s) that had triggered the disease can be important references. In order to accurately comprehend these factors, an interview needs to be conducted by a highly skilled specialist in psychiatric medicine for approximately 1 hour. Further, it should be confirmed that a patient does not have any major abnormalities in terms of general physical or neurological conditions. If necessary, the possibility of the existence of organic brain disorders is to be eliminated by electroencephalography or brain imaging tests. The patient is then subjected to diagnosis.

In various aspects, diagnosed comprises the use of one or more of Adolescent Inventory of Suicide Orientation-30 (ISO-30), Adult Suicidal Ideation Questionnaire (ASIQ), Beck Hopelessness Scale (BHS), Beck Scale for Suicide Ideation (BSS), Child Suicide Risk Assessment (CSRA), Child-Adolescent Suicidal Potential Index (CASPI), Columbia Classification Algorithm of Suicide Assessment (C-CASA), Columbia Suicide Severity Rating Scale (C-SSRS), Coping Inventory for Stressful Situations (CISS), Firestone Assessment of Self-Destructive Thoughts (FAST), Lazurus' BASIC ID tool, Lifetime Parasuicide Count (LPC), MAST—Attraction to Death (MAST-AD), MAST—Repulsion by Life (MAST-RL), Modified SAD PERSONS Scale of Hockberger and Rothstein, Multi-Attitude Suicide Tendency Scale (MAST), Parasuicide History Interview (PHI), Positive and Negative Suicide Ideation Inventory (PANSI), Reasons for Living Inventory (RFL; either long form or short form), Reasons for Living Inventory for Adolescents (RFL-A), Reasons for Living Inventory for Young Adults (RFL-YA), Risk Factors of Powell et al for Predicting the Risk of Suicide in a Psychiatric Ward Inpatient, Risk-Rescue Rating (of Weisman and Worden for Suicide Assessment), Scale for Suicidal Ideation (SSI), Suicidal Behavior History Form (SBHF), Suicidal Behavior Questionnaire for Children (SBQ-C), Suicidal Ideation Questionnaire (SIQ), Suicidal Tendencies Test, Suicide Behaviors Questionnaire (SBQ), Suicide Behaviors Questionnaire-Revised (SBQ-R), Suicide Probability Scale (SPS), and Suicide Resilience Inventory-25 (SRI-25).

In various aspects, a medical practitioner, including, but not limited to, a psychiatrist, medical doctor, psychologist, licensed social worker, nurse, physician assistant, professional counselor, or substance abuse counselor, can use a "depression symptoms rating scale". The term "depressions symptoms rating scale" means any one of a number of standardized questionnaires, clinical instruments, or symptom inventories utilized to measure symptoms and symptom severity in depression. Such rating scales are often used in clinical practice to assess a subject or assist in providing a diagnosis. Such rating scales are often used in clinical studies to define treatment outcomes, based on changes from the study's entry point(s) to endpoint(s). In further aspect, a depression symptoms rating scale comprises one or more of Apathy Scale of Glenn et al., Bech-Rafaelsen Melancholia Scale, Beck Depression Inventory (BDI), Beck Depression Inventory II (BDI-II), Brief Screening Instrument of Fabacher et al to Detect Depression in an Elderly Patient in the Emergency Department (ED-DSI), Burns Depression Checklist (BDC), Center for Epidemiologic Studies Depression Scale—Revised (CESD-R), Center for Epidemiologic Studies Depression Scale (CES-D), Center for Epidemiological Studies Depression Scale for Children (CES-DC), Children's Depression Inventory (CDI), Children's Depression Rating Scale, Revised (CDRS-R), Clinical Global Impression Scale-I, Clinician Administered Posttraumatic Stress Disorder (PTSD) Scale-2 (CAPS), Cornell Scale for Depression in Dementia (CSDD), Depression and Anxiety in Youth Scale (DAYS), Depression Anxiety Stress Scales (DASS), Depression Outcomes Module (DOM), Diagnostic and Statistical Manual of Mental Disorders 4th Edition (DSM IV), Edinburgh Postnatal Depression Scale (EPDS), Geriatric Depression Scale (GDS; long or short format), Global Assessment of Functioning Scale, Goldberg Depression & Mania Scales, Hamilton Anxiety Rating Scale, Hamilton Depression Rating Scale (HDRS), Hamilton Depression Scale (HAM-D), Harvard National Depression Screening Scale (HANDS), Hospital Anxiety and Depression Scale (HADS), International Statistical Classification of Diseases and Related Health Problems 10th Revision (ICD-10), K-SADS Depression Rating Scale (K-DEP), KSADS Lifetime and Present (KSADS-PL) schedule, Liebowitz Social Anxiety Scale, Major Depression Inventory (MDI), Medical Outcomes Study Depression Questionnaire, Mehrabian Trait Anxiety and Depression Scales, Mini-Mental State Examination, Montgomery-Asberg Depression Rating Scale, Multiscore Depression Inventory (MDI), Multiscore Depression Inventory for Children (MDI-C), Newcastle Diagnostic and ECT Scales of Carney et al for Depression, Online Depression Screening Test (ODST), Panic Disorder Severity Scale, Postpartum Depression Screening Scale (PDSS), Post-Stroke Depression Rating Scale of Gainotti et al, RAND Self Administered Depression Screener, Raskin Scale or Three-Area Severity of Depression Scale, Revised Hamilton Rating Scale for Depression (RHRSD), Reynolds Adolescent Depression Scale (RADS), Reynolds Adolescent Depression Scale, Second Edition (RADS-2), Reynolds Child Depression Scale (RCDS), Risk Factors of Beck for Postpartum Depression (PPD), Risk Factors of Kivela et al for Predicting Chronic Depression in the Elderly, Sheehan Disability Scale, Treatment Outcome PTSD Scale, Yale-Brown Obsessive Compulsive Scale, and Zung Self-Rated Depression Scale. In a yet further aspect, the depression symptoms rating scale comprises a new edition, revision or update to one of the above depression symptoms rating scales.

In various aspects, a medical practitioner, including, but not limited to, a psychiatrist, medical doctor, psychologist, licensed social worker, nurse, physician assistant, professional counselor, or substance abuse counselor, can use a "suicide symptoms rating scale". The term "suicide symptoms rating scale" means any one of a number of standardized questionnaires, clinical instruments, or symptom inventories utilized to measure symptoms and symptom severity in depression. Such rating scales are often used in clinical practice to assess a subject or assist in providing a diagnosis. Such rating scales are often used in clinical studies to define treatment outcomes, based on changes from the study's entry point(s) to endpoint(s). In further aspect, a suicide symptoms rating scale comprises one or more of Adolescent Inventory of Suicide Orientation-30 (ISO-30), Adult Suicidal Ideation Questionnaire (ASIQ), Beck Hopelessness Scale (BHS), Beck Scale for Suicide Ideation (BSS), Child Suicide Risk Assessment (CSRA), Child-Adolescent Suicidal Potential Index (CASPI), Columbia Classification Algorithm of Suicide Assessment (C-CASA), Columbia Suicide Severity Rating Scale (C-SSRS), Coping Inventory for Stressful Situations (CISS), Firestone Assessment of Self-Destructive Thoughts (FAST), Lazurus' BASIC ID tool, Lifetime Parasuicide Count (LPC), MAST—Attraction to Death (MAST-AD), MAST—Repulsion by Life (MAST-RL), Modified SAD PERSONS Scale of Hockberger and Rothstein, Multi-Attitude Suicide Tendency Scale (MAST), Parasuicide History Interview (PHI), Positive and Negative Suicide Ideation Inventory (PANSI), Reasons for Living Inventory (RFL; either long form or short form), Reasons for Living Inventory for Adolescents (RFL-A), Reasons for Living Inventory for Young Adults (RFL-YA), Risk Factors of Powell et al for Predicting the Risk of Suicide in a Psychiatric Ward Inpatient, Risk-Rescue Rating (of Weisman and Worden for Suicide Assessment), Scale for Suicidal Ideation (SSI), Suicidal Behavior History Form (SBHF), Suicidal Behavior Questionnaire for Children (SBQ-C), Suicidal Ideation Questionnaire (SIQ), Suicidal Tendencies Test, Suicide Behaviors Questionnaire (SBQ), Suicide Behaviors Questionnaire-Revised (SBQ-R), Suicide Probability Scale (SPS), and Suicide Resilience Inventory-25 (SRI-25). In a still further aspect, a suicide symptom rating scale comprises a revision, new edition, or derivation of one of a suicide symptom rating scale. In a yet further aspect, the suicide symptoms rating scale comprises a new edition, revision or update to one of the above suicide symptoms rating scales.

In various aspects, $^{31}$P-MRS spectra are acquired from the patient to determine PCr levels. In a still further aspect, the $^{31}$P-MRS spectra show an increase in PCr levels in the patient upon treatment with at least one creatine or creatine analog, at least one omega-3 fatty acid, and citicoline. In an even further aspect, the increase in PCr levels in the patient is detected after about 1-4 weeks of treatment with at least one creatine or creatine analog, at least one omega-3 fatty acid, and citicoline. In a further aspect, the increase in PCr levels in the patient is maintained for at least one week upon discontinuation of treatment with at least one creatine or creatine analog, at least one omega-3 fatty acid, and citicoline. In a still further aspect, the PCr levels continues to increase for at least one week in the patient upon discontinuation of treatment with at least one creatine or creatine analog, at least one omega-3 fatty acid, and citicoline. In an even further aspect, there is no change significant change in β-NTP levels, pH or PCr/β-NTP ratio in the patient upon treatment with at least one creatine or creatine analog, at least one omega-3 fatty acid, and citicoline. In a further aspect, there is no significant difference in the patient in the β-NTP levels, pH or PCr/β-NTP ratio compared to a normal subject. In an even further aspect, the patient has suicidal ideation.

In various aspects, $^{31}$P-MRS spectra are acquired from a patient to determine one or more of β-NTP levels, total phosphorus levels, phosphomonoester levels, phosphodiester levels, phosphocholine levels, and pH, In a further aspect, a patient's CDRS-R score is positively correlated with baseline pH. In a still further aspect, a patient's a patient's CDRS-R score is negatively correlated with β-NTP concentration. In a yet further aspect, a patient's pre-treatment β-NTP concentration is not lower than a non-depressed patient. In an even further aspect, the patient's β-NTP levels, pH or PCr/b-NTP ratio do not change with treatment using at least one creatine or creatine analog, at least one omega-3 fatty acid, and citicoline. In an even further aspect, the patient has suicidal ideation.

d. Agemts Having a Side Effect of Causing Depression

In various aspects, the agent known to have a side effect of causing depression is selected from an anticonvulsant, a barbiturate, a benzodiazepine, a β-adrenergic blocker, a calcium channel blocker, an estrogen, a fluoroquinolone, an interferon alpha, an opiod, and a statin. In a further aspect, the agent known to have a side effect of causing depression, suicide or suicidal ideation is selected from Abilify® (aripiprazole), Accutane® (isotretinoin), Ambien® (zolpidem), Antabuse®(disulfiram), Chantix® (varenicline), Lariam® (mefloquine), Norplant® (levonorgestrel Implant), Parlodel® (bromocriptine), Savella® (milnacipran), Singulair® (montelukast), Strattera® (atomoxetine), tetrabenazine, tramadol, and Zovirax® (acyclovir). In a still further aspect, the agent known to have a side effect of causing depression, suicide or suicidal ideation is selected from Adderall® (amphetamine and dextroamphetamine), Benzedrine® (amphetamine sulfate), Concerta® (methylphenidate), Cylert® (pemoline), Daytrana® (methylphenidate), Desoxyn® (methamphetamine), Dexedrine® (dextroamphetamine), Dextrostat® (dextroamphetamine), Equasym® (methylphenidate), Focalin® (dexmethylphenidate), Metadate® (methylphenidate), Methylin® (methylphenidate hydrochloride), Provigil® (modafinil), Ritalin® (methylphenidate), and Vyvanse® (lisdexamphetamine). In a further aspect, the agent known to have a side effect of causing depression, suicide or suicidal ideation is selected from Tegretol® (carbamazepine), Klonopin® (clonazepam), Depakote® (divalproex), Depakene® (valproic acid), Zarontin® (ethosuximide), Peganone® (ethotoin), Felbatol® (felbamate), Neurontin® (gabapentin), Lamictal® (lamotrigine), Vimpat® (lacosamide), Keppra® (levetiracetam), Mesantoin® (mephenytoin), Celontin® (methsuximide), Trileptal® (oxcarbazepine), Dilantin® (phenytoin), Lyrica® (pregabalin), Mysoline® (primidone), Gabitril® (tiagabine), Topamax® (topiramate), Tridione® (trimethadione), and Zonegran® (zonisamide). In a further aspect, the agent known to have a side effect of causing depression, suicide or suicidal ideation is selected from Elavil® (amitriptyline HCI), Prozac® (fluoxetine), Zoloft® (sertraline), Paxil® (paroxetine), Luvox® (fluvoxamine), Celexa® (citalopram), Lexapro® (escitalopram), Wellbutrin® (bupropion), Effexor® (venlafaxine), Serzone® (nefazodone), Remeron® (mirtazapine), and Norpramin® (desipramine).

e. Agents Known to Treat a Depression Disorder

In various aspects, the agent known to treat a depression disorder is selected from selective serotonin reuptake inhibitor, serotonin-norepinephrine reuptake inhibitors, tricyclic antidepressants, tetracyclic antidepressants, phenylpiperazine antidepressants, monoamine oxidase inhibitors, and atypical antidepressants. In a further aspect, the agent known to treat a depression disorder is selected from fluoxetine, escitalopram, citalopram, paroxetine, fluvoxamine, sertraline, venlafaxine, desvenlafaxine, duloxetine, milnacipran, amoxapine, imipramine, trimipramine, nortriptyline, clomipramine, amitriptyline, doxepin, protriptyline, desipramine, tranylcypromine, isocarboxazid, selegiline, and phenelzine. In a still further aspect, the agent known to treat a depression disorder is selected from venlafaxine, desvenlafaxine, duloxetine, and milnacipran. In yet a further aspect, the agent known to treat a depression disorder is selected from amoxapine, imipramine, trimipramine, nortriptyline, clomipramine, amitriptyline, doxepin, protriptyline, and desipramine. In an even further aspect, the agent known to treat a depression disorder is selected from tranylcypromine, isocarboxazid, selegiline, and phenelzine. In a still further aspect, the agent known to treat a depression disorder is selected from mirtazapine, maprotiline, bupropion, aripiprazole, ziprasidone, and agomelatine. In yet a further aspect, the agent known to treat a depression disorder is a selective serotonin reuptake inhibitor.

In a further aspect, the agent know to treat a depression disorder is selected from serotonin-2 antagonist/reuptake inhibitors, alpha-2 antagonists plus serotonin-2 and serotonin-3 antagonists, serotonin/norepinephrine/dopamine reuptake inhibitors, norepinephrine and dopamine reuptake inhibitors and other antidepressants.

Typically, an agent is administered in an effective amount, per its normal dosing instructions. In one aspect, the effective amount is a therapeutically effective amount. In a further aspect, the effective amount is a neutraceutically effective amount. In a still further aspect, the effective amount is a prophylactically effective amount. In yet a further aspect, the effective amount is a synergistically effective amount; for example, when combined with at least one creatine or creatine analog, at least one omega-3 fatty acid, and citicoline, in certain aspects, the agent can be employed in therapeutically effective amounts that are lower than the amount indicated in its normal dosing instructions.

3. Combination Therapeutics

In various aspects, the invention relates to a method for the treatment of a depression disorder in a subject, the method comprising administering to the subject at least one creatine or creatine analog, at least one omega-3 fatty acid, and citicoline; wherein at least one creatine or creatine analog, at least one omega-3 fatty acid, and citicoline are together administered in an effective amount. In a further aspect, at least one of the creatine or creatine analog, the omega-3 fatty acid, or citicoline is administered in an individually effective amount.

In various aspects, the methods and compositions of the invention relate to the use of at least one creatine or creatine analog, at least one omega-3 fatty acid, and citicoline to increase the efficacy of a selective serotonin reuptake inhibitor. In a further aspect, the activity of a selective serotonin reuptake inhibitor is enhanced in an individual in need thereof. In a further aspect, the method comprises co-administering to the individual at least one creatine or creatine analog, at least one omega-3 fatty acid, citicoline, and a selective serotonin reuptake inhibitor, wherein the at least one creatine or creatine analog, at least one omega-3 fatty acid, and citicoline are administered in an effective amount sufficient to normalize depression or anxiety symptoms in the individual, thereby resulting in greater activity of the selective serotonin reuptake inhibitor in the individual than would occur in the absence of co-administration of the at least one creatine or creatine analog, at least one omega-3 fatty acid, and citicoline. In a further aspect, the selective serotonin reuptake inhibitor is citalopram, escitalopram, flouxetine, fluvoxamine, paroxetine, sertraline, trazodone, venlafaxine, mirtazepine, clomipramine, or combinations with other psychotropic medications including an anti-psychotic, an anti-convulsant, a tricyclic antidepressant, a monoamine oxidase inhibitor, a selective serotonin reuptake inhibitor, a selective serotonin-norepinephrine reuptake inhibitor, a norepinephrine dopamine reuptake inhibitor, a serotonin-2 antagonist reuptake inhibitor, a benzodiazepine, a wakefulness promoting agent, anti-manic agent, or a combination of one or more of the foregoing. In a further aspect, co-administered comprises administering the at least one creatine or creatine analog, at least one omega-3 fatty acid, and citicoline at the same time as the selective serotonin reuptake inhibitor. In a yet further aspect, co-administering comprises administering the at least one creatine or creatine analog, at least one omega-3 fatty acid, and citicoline at a different time than the selective serotonin reuptake inhibitor.

In various aspects, the invention relates to an oral dosage form comprising at least one creatine or creatine analog, at least one omega-3 fatty acid, citicoline, and one or more of at least one agent known to treat a depression or anxiety disorder; or at least one agent known to have a side effect of causing depression or anxiety.

4. Improving Neuropsychological Performance

In one aspect, the invention relates to a method for improving neuropsychological performance in a subject, the method comprising administering to the subject at least one creatine or creatine analog, at least one omega-3 fatty acid, and citicoline; at least one creatine or creatine analog, at least one omega-3 fatty acid, and citicoline are together administered in an effective amount. In a further aspect, at least one of the creatine or creatine analog, the omega-3 fatty acid, or citicoline is individually administered in an effective amount.

In a further aspect, neuropsychological performance is memory. In a still further aspect, neuropsychological performance is verbal memory. In yet a further aspect, neuropsychological performance is visuospatial memory.

In a further aspect, the subject is a patient. In a still further aspect, the subject is a healthy individual. In yet a further aspect, the subject is a female. In an even further aspect, the subject is an adult. In a still further aspect, the adult is from about 40 years of age to about 60 years of age.

In a further aspect, the subject has been diagnosed with a need for improved neuropsychological performance prior to the administering step. In a further aspect, the method further comprises the step of identifying a subject in need of improved neuropsychological performance.

In a further aspect, the effective amount is a neutraceutically effective amount. In a still further aspect, the effective amount is a therapeutically effective amount.

5. Improving Complexion

In one aspect, the invention relates to a method of improving complexion in a subject, the method comprising administering to the subject at least one creatine or creatine analog, at least one omega-3 fatty acid, and citicoline; wherein at least one creatine or creatine analog, at least one omega-3 fatty acid, and citicoline are together administered in an effective amount. In a further aspect, at least one of the creatine or creatine analog, the omega-3 fatty acid, or citicoline is individually administered in an effective amount.

In a further aspect, the effective amount is a neutraceutically effective amount. In a still further aspect, the effective amount is a therapeutically effective amount.

6. Use of Compositions

Also provided are the uses of at least one creatine or creatine analog, at least one omega-3 fatty acid, and citicoline. In various aspects, the use relates to the improvement of neuropsychological performance in a subject. In various aspects, the use relates to the treatment of a depression disorder in a subject. In various aspects, the use relates to the reduction of the likelihood of a depression or anxiety symptom in a subject. In various further aspects, the use relates to the improvement of complexion in a subject.

7. Kits

In one aspect, the invention relates to a kit comprising: a) at least one creatine or creatine analog; b) at least one omega-3 fatty acid; c) and citicoline.

In a further aspect, the kit further comprises one or more of: a) at least one agent known to treat a depression or anxiety disorder; b) at least one agent known to have a side effect of causing depression or anxiety; c) at least one agent known to modify neuropsychological performance; d) at least one agent known to have a side effect of modifying neuropsychological performance; e) instructions for treating a disorder associated with depression or anxiety; or f) instructions for modifying neuropsychological performance. In a still further aspect, modify is to increase. In yet a further aspect, modify is to decrease.

In a further aspect, the kit further comprises one or more of: a) at least one agent known to modify complexion; b) at least one agent known to have a side effect of modifying complexion; or c) instructions for modifying complexion. In a still further aspect, modify is to improve. In yet a further aspect, modify is to worsen.

In a further aspect, the at least one creatine or creatine analog, at least one omega-3 fatty acid, and citicoline are co-packaged. In a still further aspect, the at least one creatine or creatine analog, at least one omega-3 fatty acid, and citicoline are co-formulated. In yet a further aspect, the at least one creatine or creatine analog and at least one omega-3 fatty acid are co-packaged. In an even further aspect, the at least one creatine or creatine analog and at least one omega-3 fatty acid are co-formulated. In a still further aspect, the at least one creatine or creatine analog and citicoline are co-packaged. In yet a further aspect, the at least one creatine or creatine analog and citicoline are co-formulated. In an even further aspect, the at least one omega-3 fatty acid and citicoline are co-packaged. In a still further aspect, the at least one omega-3 fatty acid and citicoline are co-formulated.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

8. Manufacture of a Medicament

In one aspect, the invention relates to a method for the manufacture of a medicament for treatment of depression disorder in a subject, the method comprising combining at least one creatine or creatine analog, at least one omega-3 fatty acid, and citicoline, wherein at least one creatine or creatine analog, at least one omega-3 fatty acid, and citicoline are administered in an effective amount, alone or in combination with another agent, with a pharmaceutically acceptable carrier or diluent. In a further aspect, at least one of the creatine or creatine analog, the omega-3 fatty acid, or citicoline is administered in an effective amount.

In one aspect, the invention relates to a method for the manufacture of a medicament for improving neuropsychological performance in a subject, the method comprising combining at least one creatine or creatine analog, at least one omega-3 fatty acid, and citicoline, wherein at least one creatine or creatine analog, at least one omega-3 fatty acid, and citicoline are administered in an effective amount, alone or in combination with another agent, with a pharmaceutically acceptable carrier or diluent. In a further aspect, at least one of the creatine or creatine analog, the omega-3 fatty acid, or citicoline is administered in an effective amount.

In one aspect, the invention relates to a method for the manufacture of a medicament for improving complexion in a subject, the method comprising combining at least one creatine or creatine analog, at least one omega-3 fatty acid, and citicoline, wherein at least one creatine or creatine analog, at least one omega-3 fatty acid, and citicoline are administered in an effective amount, alone or in combination with another agent, with a pharmaceutically acceptable carrier or diluent. In a further aspect, at least one of the creatine or creatine analog, the omega-3 fatty acid, or citicoline is administered in an effective amount.

9. Non-Medical Uses

Also provided are the uses of the disclosed compounds and products as pharmacological tools in the development and standardization of in vitro and in vivo test systems for the evaluation of the effects of therapeutic agents to treat depression disorders in laboratory animals such as cats, dogs, rabbits, monkeys, rats and mice, as part of the search for new therapeutic agents of depression disorders. In a further aspect, the invention relates to the use of a disclosed compound or a disclosed product as pharmacological tools in the development and standardization of in vitro and in vivo test systems for the evaluation of the effects of potentiators of depression disorders in laboratory animals such as cats, dogs, rabbits, monkeys, rats and mice, as part of the search for new therapeutic agents of depression disorders.

I. References

Alexander Gene E; Ryan, Lee; Bowers, Dawn; Foster, Thomas C; Bizon, Jennifer L; Geldmacher, David S; Glisky, Elizabeth L; Characterizing cognitive aging in humans with links to animal models. Frontiers in Aging Neuroscience, Volume 4, Article 21, September, 2012.

Beard, E; Braissant, O; Synthesis and transport of creatine in the CNS: importance for cerebral function. Journal of Neurochemistry 115: 297-313, 2010.

Chudasama, Y; Animal models of prefrontal-executive function. Behavioral Neuroscience 123: 327-343, 2011.

Eckert, Gunter P; Lipka, Uta; Muller, Walter E; Omega-3 fatty acids in neurodegenerative disease: Focus on mitochondria. Prostaglandins, Leukotrienes, and Essential Fatty Acids 88: 105-114, 2013.

Floresco, Stan B; Jentsch, James D; Phamacological enhancement of memory and executive functioning in laboratory animals. Neuropsychopharmacology 36: 227-250, 2011.

Hunsaker, Michael R; The importance of considering all attributes of memory in behavioral endophenotyping of mouse models of genetic disease. Behavioral Neuroscience 126: 371-380, 2012.

Institute of Medicine Consensus Report; Chimpanzees in biomedical and behavioral research: Assessing the necessity. Dec. 15, 2011.

Keeler, J F; Robbons T W, Translating cognition from animals to humans. Biochemical Pharmacology 81: 1356-1366, 2011.

Kesner, Raymond P; Churchwell, John C; An analysis of rat prefrontal cortex in mediating executive function, Neurobiology of learning and memory 96: 417-435, 2011.

McGonigle, P; Animal models of CNS disorders. Biochemical Pharmacology (2013), http://dx.doi.org/10.1016/j.bcp.2013.06.016

Silveri, M M; Dikan, J; Ross, A J; Jensen, J E; Kamiya, T; Kawada, Y; Renshaw, P F; Yurgelun-Todd, D A; Citicoline enhances frontal lobe bioenergetics as measured by phosphorus magnetic resonance spectroscopy. NMR in Biomedicine 21: 1066-75, 2008.

J. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Study Methods

Approval for the study was obtained from the University of Utah Institutional Review Board (IRB). Informed consent consisted of written assent from participants. The study was conducted under U.S. Food and Drug Administration (FDA) Investigational New Drug Application #104,586. An external Data Safety and Monitoring Board vested with authority to halt the trial was established, and the study was conducted in accordance of the principles of Good Clinical Practice (GCP).

Participants were recruited through self-referral and IRB-approved advertising. Consecutive patients who met inclusion criteria were enrolled. Inclusion criteria included the following: females between 40-60 years of age. The study's exclusion criteria were: significant medical condition, history of co-morbid psychiatric disorders, current Axis I or II diagnosis, part participation in a pharmacotherapeutic trial, head injury with a loss of consciousness (LOC) of >5 min, use of psychotropic medication, a history of fish allergies, a medical condition associated with clinically significant decreases in coagulability, and use of anticoagulant medication.

Diagnoses were excluded based on a Mini-International Psychiatric Interview (M.I.N.I) (Sheehan et al., 1998) and a medical exam. A complete blood count, metabolic panel, lipid profile, thyroid stimulating hormone, urinalysis and urine microalbumin were obtained to establish that participants were in generally good health, and to rule out the presence of undiagnosed medical conditions. The laboratory studies were repeated at the conclusion of treatment, to prospectively identify any abnormalities associated with creatine administration.

Participants were given a fixed-dose Creapure® brand of creatine monohydrate (AlzChem LLC, Trostberg, Germany) 5 grams, Kyowa Hakko brand of CDP-choline 500 milligrams, and OmegaBrite brand of omega-3 fatty acids 2 grams by mouth daily for 4 weeks. At each study visit, the following rating scales were administered: the Hamilton Anxiety Rating Scale (HAM A) (Hamilton, 1969) and the Hamilton Depression Rating Scale (HAM D) (Hamilton, 1960), the California Verbal Learning Test (Delis et al., 1987) and the Rey Osterrieth Figure Test (Bennett-Levy, 1984). Adverse events we recorded at each study visit.

As an active control a dose of 250 of or 500 mg of CDP-choline was administered to healthy volunteers.

2. Clinical Results

Summary results for each study participant are presented in Table 1 below. The participants consisted of 19 Caucasian females and one Hispanic female. None of the participants initiated or terminated psychosocial treatment during the study. Twenty-two participants completed the full four weeks of treatment with creatine, citicoline, and omega-3 fatty acids. No participant withdrew from the study due to treatment emergent adverse effects or lack of efficacy.

Participants in the CCO group evidenced fewer anxious symptom compared to participants in the placebo group. Specifically, participants in the CCO group had less anxious symptomatology on the Hamilton Anxiety Rating Scale (HAM-A) at two weeks compared to participants in the placebo group (t=1.85, p=0.07). The HAM-A and HAM-D were not collected at baseline during the CDP-choline, creatine, omega-3 fatty acids.

TABLE 1

Visit 2 HAM-A and HAM-D Scores for Each Group

| | 250 mg CDP-Choline | | 500 mg CDP-Choline | | Placebo | | CCO[a] | |
|---|---|---|---|---|---|---|---|---|
| | Mean | STD | Mean | STD | Mean | STD | Mean | STD |
| HAM-A[b] | 1.80 | 2.09 | 1.35 | 1.35 | 2.50 | 3.46 | 0.60 | 1.23 |
| HAM-D[c] | 1.60 | 1.67 | 1.35 | 1.23 | 1.80 | 1.96 | 0.75 | 1.62 |

[a]CCO is creatine, citicoline, and omega-3;
[b]HAM-A is the Hamilton Anxiety Rating Scale. A higher score indicates more severe symptoms;
[c]HAM-D is the Hamilton Depression Rating Scale. A higher score indicates more severe symptoms.

Summary results for the placebo group compared to active control groups, and treatment groups are presented in Table 2 below.

TABLE 2

Visit 2 HAM-A and HAM-D Scores for Placebo Compared to the Remaining Groups

| | 250 mg CDP-Choline | | 500 mg CDP-Choline | | CCO[a] | |
|---|---|---|---|---|---|---|
| | $F_{(1,38)}$ | p-value | $F_{(1,38)}$ | p-value | $F_{(1,38)}$ | p-value |
| HAM-A[b] | 0.60 | 0.443 | 1.92 | 0.174 | 5.36 | 0.026 |
| HAM-D[d] | 0.12 | 0.730 | 0.76 | 0.390 | 3.41 | 0.073 |

[a]CCO is creatine, citicoline, and omega-3;
[b]HAM-A is the Hamilton Anxiety Rating Scale. A higher score indicates more severe symptoms;
[c]HAM-D is the Hamilton Depression Rating Scale. A higher score indicates more severe symptoms.

3. Neuropsychological Performance

Methods for evaluating the neuropsychological performance are known in the art. Exemplary methods for gauging neuropsychological performance include the California Verbal Learning Test (CVLT), the Rey Osterrieth Complex Figure Test (ROCFT), the WAIS Block Design Subtest, the Judgment of Line Orientation, the Hooper Visual Organization Test, the Wechsler Memory Scale (WMS), the WMS-III Verbal Memory Index, the Rey Auditoring Verbal Learning Test, the Verbal Selective Reminding Test, the Hopkins Verbal Learning Test, the Nonverbal Selective Reminding Test, the Continuous Recognition Memory Test, and the Visuo-Motor Integration Test. Enhancement can be measured, for example, relative to a control group, such as a group that did not receive a disclosed composition.

a. Verbal Memory

Table 3 below displays the California Verbal Learning Test mean scores for study participants at 4 weeks. Subjects in the CCO group recalled more words on the California Verbal Learning Test List B between one and four weeks when compared to participants in the placebo group (F=6.08, p<0.05). The data for CVLT List A Trial 1 and CVLT Trials 1-5 are depicted graphically in FIG. 1A. Data for CVLT Long Delay is illustrated in FIG. 1B.

TABLE 3

Visit 3 California Verbal Learning Test (CVLT)

| | Placebo | | CCO | | | |
|---|---|---|---|---|---|---|
| | Mean | STD | Mean | STD | $F_{(1,38)}$ | p-value |
| CVLT List A Trial 1 | 9.70 | 2.6 | 11.25 | 2.3 | 3.87 | 0.057 |

TABLE 3-continued

Visit 3 California Verbal Learning Test (CVLT)

| | Placebo | | CCO | | | |
|---|---|---|---|---|---|---|
| | Mean | STD | Mean | STD | $F_{(1,38)}$ | p-value |
| CVLT Trials 1-5 | 62.05 | 8.1 | 67.85 | 7.8 | 5.35 | 0.026 |
| CVLT Long Delay | 13.45 | 2.3 | 14.60 | 1.8 | 3.03 | 0.090 | b. Visuospatial Memory

Figure 2:
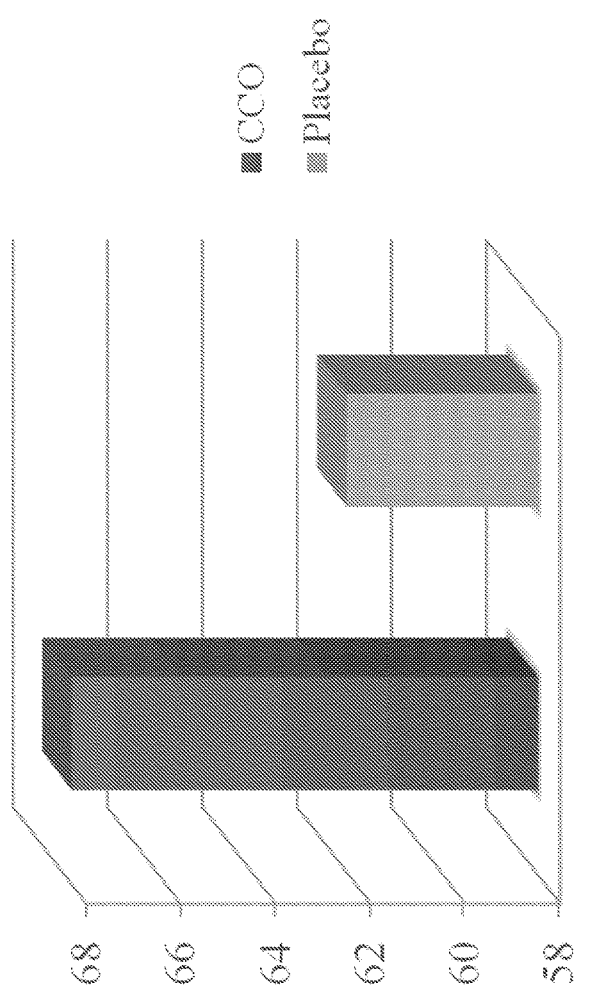
FIG. 2 shows representative data pertaining to improved verbal memory observed in response to the combined use of citicoline, creatine, and omega-3.
Figure 3:
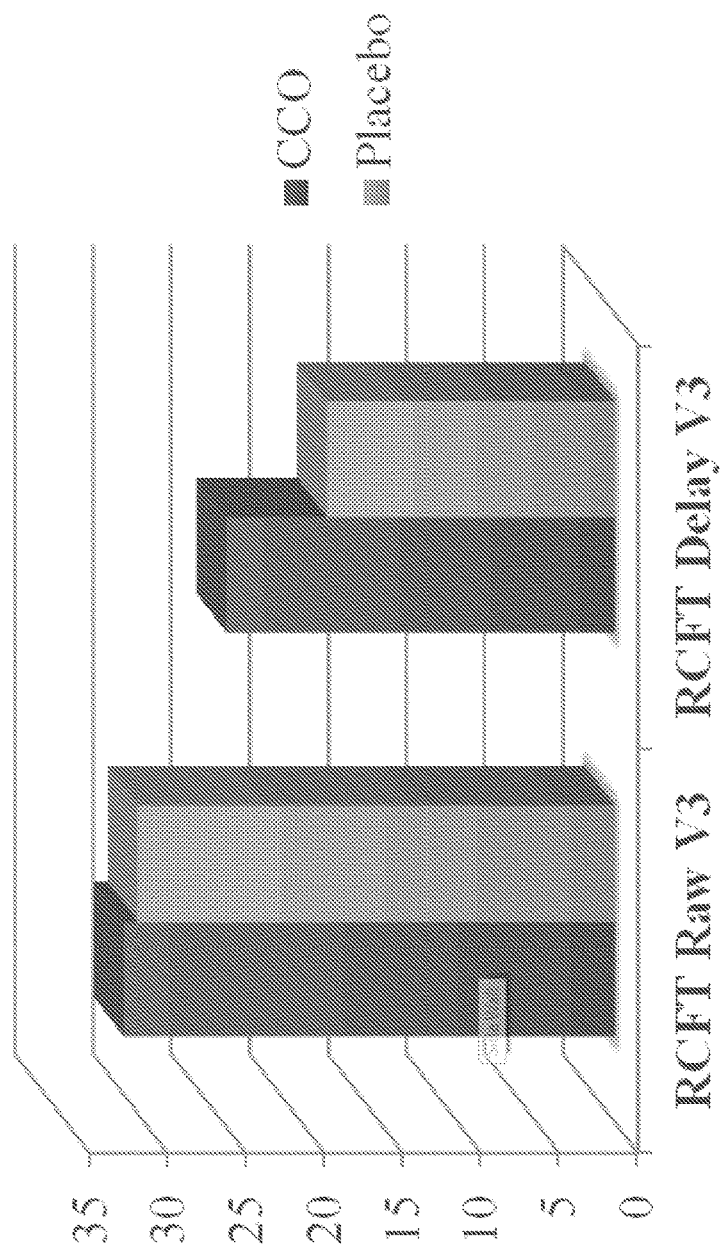
FIG. 3 shows representative data pertaining to the effect of citicoline, creatine, and omega-3 on visuospatial memory.
Figure 4:
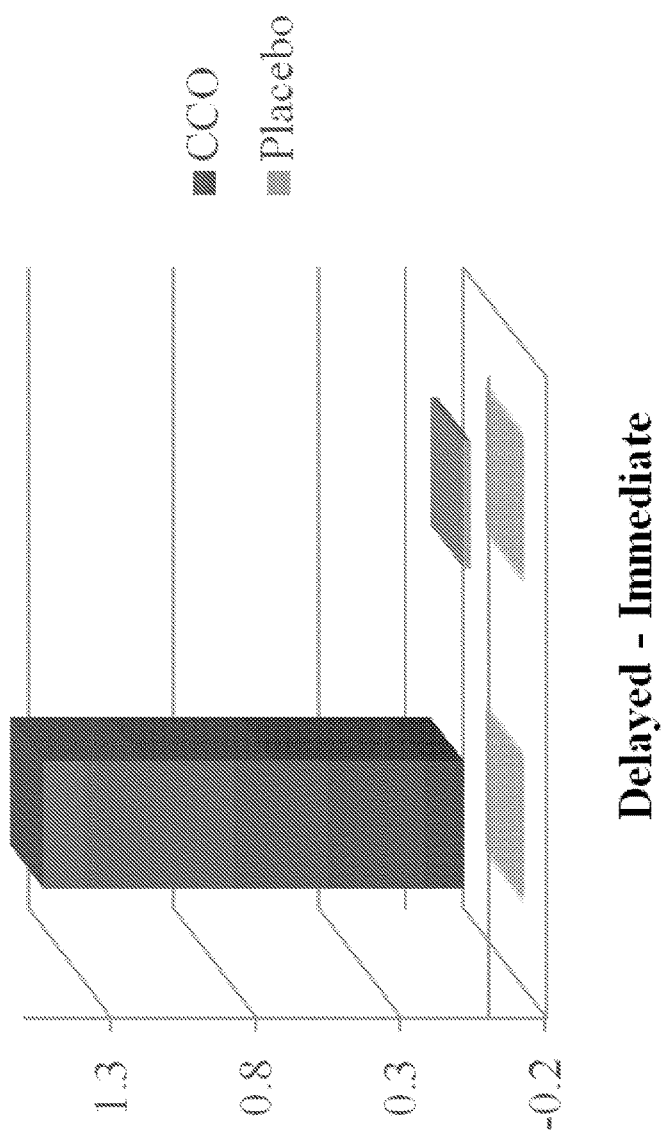
FIG. 4 shows representative data pertaining to improved visuospatial memory observed in response to the combined use of citicoline, creatine, and omega-3.

Table 4 below displays the Rey Osterrieth Complex Figure Test (ROCFT) mean scores for study participants at 4 weeks. The data for immediate raw and delayed raw are depicted graphically in FIG. 2A. The data for immediate raw is illustrated in FIG. 2B

TABLE 4

Visit 3 Rey Osterrieth Complex Figure Test (ROCFT)

| | Placebo | | CCO | | | |
|---|---|---|---|---|---|---|
| | Mean | STD | Mean | STD | $F_{(1,38)}$ | p-value |
| Immediate Raw | 30.48 | 4.4 | 31.40 | 3.1 | 15.19 | <0.001 |
| Delayed Raw | 18.43 | 7.5 | 24.83 | 4.7 | 10.29 | 0.003 |
| Delayed-Immediate | −0.02 | 2.2 | 1.45 | 2.9 | 3.72 | 0.078 |

4. Adverse Events Associated with Citicoline, Creatine, and Omega-3 Treatment

At the fixed dose of 5 grams (creatine), 500 milligrams (citicoline), and 2 grams (omega-3 fatty acids), the treatment was well tolerated by study participants. Adverse events, are summarized in Table 5 below. There were no Serious Adverse Events (SAEs) (Food and Drug Administration 1996).

Participants' vital signs were recorded at each study visit. No statistically significant changes in weight, blood pressure or heart rate were found. Although not measured systematically, participant acceptance of creatine, citicoline, and omega-3 fatty acids as a treatment intervention appeared good, and there were no premature terminations due to concerns about the study drug. The laboratory tests performed at baseline and repeated after four weeks of treatment revealed no clinically significant changes or abnormalities. No participant developed microalbuminuria or a serum creatine outside the reference range in response to treatment with creatine.

TABLE 5

| Body System and Preferred System | Total N[a] | Total (%)[b] | Severity |
|---|---|---|---|
| Overall | | | |
| General | 13 | 59.1 | |
| Headache | 1 | 4.5 | Mild |
| | 1 | 4.5 | Minimal |
| Integumentary | | | |
| Flushed Skin | 1 | 4.5 | Minimal |
| Acne | 1 | 4.5 | Mild |
| Abnormal Hair Growth | 1 | 4.5 | Mild |
| Gastrointestinal | | | |
| Nausea | 3 | 13.6 | Minimal |
| | 2 | 9.1 | Mild |
| Taste Abnormality | 1 | 4.5 | Minimal |
| Diarrhea | 1 | 4.5 | Minimal |
| Abdominal Pain | 1 | 4.5 | Minimal |
| Appetite Decrease | 1 | 4.5 | Minimal |
| Flatulence | 1 | 4.5 | Mild |
| Appetite Increase | 2 | 9.1 | Mild |
| Weight Increase | 2 | 9.1 | Mild |
| Muscloskeletal | | | |
| Muscle Fatigue | 1 | 4.5 | Minimal |
| | 2 | 9.1 | Mild |
| Muscle Cramps | 1 | 4.5 | Minimal |
| Muscle Tingling | 1 | 4.5 | Mild |
| Psychological | | | |
| Irritability | 1 | 4.5 | Minimal |

[a]Number of participants experiencing an adverse event (participant was counted only once for each adverse event);
[b]Percent of the total number of participants who completed all three visits of the study (N = 22).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A neutraceutical composition comprising:
    (a) at least one creatine or creatine analog, wherein the at least one creatine or creatine analog is present in an amount from about 30 wt % to about 60 wt % of the composition;
    (b) at least one omega-3 fatty acid;
    (c) citicoline; and
    (d) optionally, a neutraceutically acceptable carrier;
    wherein at least one creatine or creatine analog, at least one omega-3 fatty acid, and citicoline are together present in a neutraceutically effective amount.

2. The composition of claim 1, wherein at least one of the creatine or creatine analog, the omega-3 fatty acid, or citicoline is present in an individually neutraceutically effective amount.

3. The composition of claim 1, wherein the at least one creatine analog is selected from creatine monohydrate, creatine ethyl ester, creatine citrate, creatine malate, creatine tartrate, and magnesium creatine chelatem, or a mixture thereof.

4. The composition of claim 1, wherein the at least one creatine or creatine analog comprises a precursor of s-adenosyl methionine.

5. The composition of claim 4, wherein the precursor is guanidinoacetate.

6. The composition of claim 1, wherein the at least one omega-3 fatty acid is present in an amount from about 20 wt % to about 40 wt % of the composition.

7. The composition of claim 1, wherein the at least one omega-3 fatty acid is selected from α-linolenic acid (ALA), eicosapentaenoic acid (EPA), and docosahexaenoic acid (DHA), or a mixture thereof.

8. The composition of claim 1, wherein the at least one omega-3 fatty acid is EPA.

9. The composition of claim 1, wherein the citicoline is present in an amount from about 10 wt % to about 40 wt % of the composition.

10. The composition of claim 1, wherein the composition is formulated for oral administration.

11. The composition of claim 1, wherein the composition comprises a neutraceutically acceptable carrier selected from maize starch, polyvinyl pyrroldiinone, hydroxypropyl methylcellulose, lactose, microcrystalline cellulose, calcium hydrogen phosphate, magnesium stearate, talc, silica, potato starch, sodium starch glycolate, and sodium lauryl sulfate.

12. A method of treating a depression disorder in a subject, the method comprising administering to the subject the composition of claim 1, wherein the depression disorder is selected from major depressive disorder, minor depression disorder, dysthymia, postpartum depression, seasonal affective disorder, bipolar disorder, mixed anxiety depression, unspecified depression, adjustment disorder, atypical depression, psychotic depression, and suicidal ideation.

\* \* \* \* \*